US011107551B2

(12) United States Patent
Buntjer et al.

(10) Patent No.: US 11,107,551 B2
(45) Date of Patent: Aug. 31, 2021

(54) DIRECTED STRATEGIES FOR IMPROVING PHENOTYPIC TRAITS

(71) Applicant: Keygene N.V., Wageningen (NL)

(72) Inventors: Jacob Bernhard Buntjer, Wageningen (NL); José Lúcio Lima Guerra, Wageningen (NL); Timotheus Gerardus Doeswijk, Wageningen (NL); Remco Van Berloo, Wageningen (NL); Niek Bouman, Wageningen (NL)

(73) Assignee: KEYGENE N.V., Wageningen (NL)

( * ) Notice: Subject to any disclaimer, the term of this patent is extended or adjusted under 35 U.S.C. 154(b) by 590 days.

(21) Appl. No.: 14/898,005

(22) PCT Filed: Jun. 13, 2014

(86) PCT No.: PCT/NL2014/050389
§ 371 (c)(1),
(2) Date: Dec. 11, 2015

(87) PCT Pub. No.: WO2014/200348
PCT Pub. Date: Dec. 18, 2014

(65) Prior Publication Data
US 2016/0132635 A1 May 12, 2016

(30) Foreign Application Priority Data

Jun. 14, 2013 (NL) .................................... 2010982

(51) Int. Cl.
*G16B 20/00* (2019.01)
*G16B 40/00* (2019.01)
*A01H 1/04* (2006.01)
*C12Q 1/6876* (2018.01)

(52) U.S. Cl.
CPC ............... *G16B 20/00* (2019.02); *A01H 1/04* (2013.01); *G16B 40/00* (2019.02); *C12Q 1/6876* (2013.01); *C12Q 2600/124* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2010/0037342 A1    2/2010   Johnson et al.

FOREIGN PATENT DOCUMENTS

| EP | 1 962 212 A1 | 8/2008 |
|---|---|---|
| EP | 2 813 141 A1 | 12/2014 |
| WO | WO 2008/074101 A2 | 6/2008 |
| WO | WO 2008/085046 A1 | 7/2008 |
| WO | WO 2010/020252 A1 | 2/2010 |
| WO | WO-2010/120844 A1 | 10/2010 |
| WO | WO 2012/075125 A1 | 6/2012 |

OTHER PUBLICATIONS

Calus, M. P. L., Meuwissen, T. H. E., de Roos, A. P. W. & Veerkamp, R. F. Accuracy of Genomic Selection Using Different Methods to Define Haplotypes. Genetics 178, 553-561 (2008).*
Goddard, M. E. Genomic selection: Prediction of accuracy and maximisation of long term response. Genetica 136, 245-257 (2009).*
Goddard, M. E. & Hayes, B. J. Genomic selection. Journal of Animal Breeding and Genetics 124, 323-330 (2007).*
Heslot, N., Yang, H.-P., Sorrells, M. E. & Jannink, J.-L. Genomic Selection in Plant Breeding: A Comparison of Models. Crop Science 52, 146 (2012).*
Jannink, J.-L. Dynamics of long-term genomic selection. Genetics Selection Evolution 42, 1-11 (2010).*
Jannink, J.-L., Lorenz, A. J. & Iwata, H. Genomic selection in plant breeding: from theory to practice. Briefings in Functional Genomics 9, 166-177 (2010).*
Kemper, K. E., Bowman, P. J., Pryce, J. E., Hayes, B. J. & Goddard, M. E. Long-term selection strategies for complex traits using high-density genetic markers. Journal of Dairy Science 95, 4646-4656 (2012).*
Li, X., Zhu, C., Wang, J. & Yu, J. Computer Simulation in Plant Breeding. Advances in Agronomy 116, 219-264 (2012).*
Long, N., Gianola, D., Rosa, G. J. M. & Weigel, K. A. Long-term impacts of genome-enabled selection. Journal of Applied Genetics 52, 467-480 (2011).*
Lorenz, A. J. et al. Genomic Selection in Plant Breeding: Knowledge and Prospects. Advances in Agronomy 110, 77-123 (2011).*
Moose, S. P. & Mumm, R. H. Molecular Plant Breeding as the Foundation for 21st Century Crop Improvement. Plant Physiology 147, 969-977 (2008).*
Acquaah, G. Principles of Plant Genetics and Breeding, Second edition; Wiley-Blackwell: Chichester, 2012. Excerpt of chapters 16-18, pp. 303-373.*
Robbins, M. D.; Staub, J. E. Comparative Analysis of Marker-Assisted and Phenotypic Selection for Yield Components in Cucumber. Theor Appl Genet 2009, 119 (4), 621-634.*
Cole et al., "Use of haplotypes to estimate Mendelian sampling effects and selection limits", Journal of Animal Breeding and Genetics, 2011, vol. 128, pp. 446-455.
Hofheinz et al., "Genome-based prediction of test cross performance in two subsequent breeding cycles", Theor. Appl. Genet., 2012, vol. 125, pp. 1639-1645.
Isidro et al., "Training set optimization under population structure in genomic selection", Theor. Appl. Genet., Nov. 2014, 14 pgs.
Wimmer et al., "Genome-wide prediction of traits with different genetic architecture through efficient variable selection", Genetics, Oct. 2013, vol. 195, pp. 573-587.

(Continued)

*Primary Examiner* — Soren Harward
(74) *Attorney, Agent, or Firm* — Foley & Lardner LLP; Sunil Talapatra

(57) ABSTRACT

The present invention provides a method for improving at least one phenotypic trait of interest in subsequent generation(s) of a population of individuals, preferably crop plants or cattle. Particularly, the method identifies the combination of at least three individuals that gives, upon subsequent intercrossing, the highest estimated probability of improving the at least one phenotypic trait of interest in the subsequent generation(s). Also provided is a computer-readable medium comprising instructions for performing the method.

14 Claims, 7 Drawing Sheets

(56) References Cited

OTHER PUBLICATIONS

Extended European Search Report issued in EP 16 19 3259 dated Dec. 23,2016.
Jiang, "Molecular markers and marker-assisted breeding in plants", Plant Breeding from Laboratories to Fields, InTech, May 2013.
Buntjer et al., "Haplotype diversity: the link between statistical and biological association." TRENDS in Plant Science, Oct. 2005, vol. 10, No. 10, pp. 466-471.
Meuwissen et al., "Prediction of total genetic value using genome-wide dense marker maps." Genetics, Apr. 2001, vol. 157, pp. 1819-1829.
Meuwissen, "Genomic Selection: the future of marker assisted selection and animal breeding." Marker Assisted Selection, Oct. 17, 2003, pp. 54-59.
Tingting et al., "Performance prediction of $F_1$ hybrids between recombinant inbred lines derived from two elite maize inbred lines." Theor. Appl. Genet., 2013, vol. 126, pp. 189-201.
Written Opinion and Search Report issued in Netherlands Patent Application No. 2010982 dated Sep. 26, 2013.
International Search Report issued in International Patent Application No. PCT/NL2014/050389 dated Sep. 11, 2014.
Bertan, et al., "Parental selection strategies in plant breeding programs". Journal of Crop Science and Biotechnology, vol. 10, No. 4, 2007, pp. 211-222.
Cole et al., "Use of haplotypes to estimate Mendelian sampling effects and selection limits". Journal of Animal Breeding and Genetics, vol. 128, Apr. 2011, pp. 446-455.
Collard et al., "Marker-assisted selection; an approach for precision plant breeding in the twenty-first century", Philosophical Transactions of The Royal Society B, vol. 363, Feb. 2008, pp. 557-572.
Hofheinz et al., "Genome-based prediction of test cross performance in two subsequent breeding cycles". Theoretical and Applied Genetics, vol. 125, Jul. 20, 2012, pp. 1639-16455.
Isidro et al., "Training set optimization under population structure in genomic selection", Theoretical and Applied Genetics, Nov. 2014, vol. 128, pp. 145-158.
Kemper et al., "Long-term selection strategies for complex traits using high-density genetic markers". Journal of Dairy Science, vol. 95, 2012, pp. 4646-4656.
Miedaner, "Grundiagen der Pflanzenzlichtung" Frankfurth/M: DLG-Verlags-GmbH, 2010. Chapter 3.3, p. 47.
A.E. Hoerl, "Optimum solution of many variables equations", Chemical Engineering Progress, 1959, vol. 55, pp. 69-78.
Haley et al., "Strategies to utilize marker-quantitative trait loci associations", Journal of Dairy Science, 1998, vol. 81, No. 2, pp. 85-97.
Hospital et al., "Efficient marker-based recurrent selection for multiple quantitative trait loci", Genet. Res., Camb., 2000, vol. 75, pp. 357-368.
Jiang, "Molecular markers and marker-assisted breeding in plants, Chapter 3", Plant Breeding from Laboratories to Fields, May 2013, pp. 45-83.
Servin et al., "Toward a theory of marker-assisted gene pyramiding", Genetics, Sep. 2004, vol. 168, pp. 513-523.
Valente et al., "Computer Note OptiMAS: A decision support tool for marker-assisted assembly of diverse alleles", Journal of Heredity, 2013, vol. 104, No. 4, pp. 586-590.
Broman, "Genotype Probabilities at Intermediate Generations in the Construction of Recombinant Inbred Lines", Genetics, vol. 190, pp. 403-412, Feb. 2012.
XVth Meeting of the EUCARPIA Section-Biometrics in Plant Breeding, Sep. 5-7, 2012.
Heffner et al., "Genomic Selection for Crop Improvement" Crop Science, vol. 49, Jan.-Feb. 2009.

\* cited by examiner

DIRECTED STRATEGIES FOR IMPROVING PHENOTYPIC TRAITS

CROSS-REFERENCE TO RELATED APPLICATIONS

This application is the National Phase of International Patent Application No. PCT/NL2014/050389, filed Jun. 13, 2014, published on Dec. 18, 2014 as WO 2014/200348 A1, which claims priority to Netherlands Patent Application No. 2010982, filed Jun. 14, 2013. The contents of which are herein incorporated by reference in its entirety.

TECHNICAL FIELD

The present invention relates to the field of methods for improving at least one phenotypic trait of interest in subsequent generation(s) of a population of individuals, preferably crop plants or cattle. Particularly, the present invention relates to methods for identifying the combination of at least three individuals that gives, upon subsequent intercrossing, the highest estimated probability of improving the at least one phenotypic trait of interest in the subsequent generation(s).

BACKGROUND OF THE INVENTION

The limitations of marker assisted selection (MAS), occurring when applied to manage quantitative variation under the influence of a large number of loci, are expected to be greatly improved by the simultaneous usage of genome wide markers. Cost effective genotyping techniques enable breeding companies to generate information about genetic variation on thousands of loci across the genome on all breeding materials a plant breeder has at his or her disposal to create new varieties. As a result, new strategies to perform plant/animal breeding in this new landscape of abundant information are emerging. One strategy is Genomic Selection (GS), the use of genome-wide genotypic data to predict estimated breeding values (EBV) for selection purposes, which was originally proposed in animal breeding [Meuwissen et al., 2001], and has since then been successfully applied in animal breeding in for instance cattle and poultry. The EBV is calculated from performance data and it is an approximation to an individual's genetic merit. In GS, EBVs are predicted based on genome wide information. GS is performed with a class of statistical methods called ridge regression. Ridge regression was first introduced in by E. A. Hoerl (1959). Ridge regression is used when ill posed problems are observed: for instance when more variables than the total number of observations are used to make a prediction. The most important parameter in ridge regression corresponds to the distribution assumed to the model parameters (GS model). This distribution is used to capture the genotype/phenotype relationship. Intense research has led to multiple distribution assumptions, which in turn has led to a large number of multiple ridge regression models, also call GS models (BayesA, BayesB, BayesC, BayesC pi, BayesD, machine learning methods, information theory methods, etc.). With ever improving statistical methods and increasing sizes of breeding data it is fair to expect that the accuracy of models capturing genotype/phenotype relationships are likely to gradually improve. And it is expected that a variety of such models will become applicable in breeding, enabling GS to become a more and more important breeding strategy.

In recent years, genomic selection has been under investigation by plant breeders as an alternative to marker assisted selection (MAS) and phenotype selection. GS as a strategy has the potential to improve highly complex traits or combinations of multiple traits without the requirement to identify significantly linked/associated loci or candidate genes by simply constructing quantitative genotype/phenotype models over a large amount of genome-wide distributed markers. Use of genome-wide estimated breeding values (GEBVs) rather than actual phenotypic values provides breeders the opportunity to select individual animals or plants for trait performance without doing actual phenotyping, thus potentially saving costs and time. This can be applied both to single, complex traits but also to multiple traits combined in an index. The possibility to estimate traits in an earlier stage is in particular advantageous in crops with a long breeding cycle (i.e. tree species), and in this way easily multiple years can be gained.

One major application of GS or methods that capture whole genotype/phenotype relationships in the breeding practice is the selection of parents for the next breeding cycle. This is done by prediction of the GEBVs for a trait or an index of traits for all members of a panel of candidate parents after which the parents with the highest values are selected for further breeding, a practice not unlike the traditional selection practice based on actual phenotypes [Haley and Visscher, 1998].

As a breeding method, prediction based strategies based on genotype/phenotype relationships works in two phases, a training phase and a selection phase:

Training Phase

In this phase, the investment is made in setting up the phenotypic prediction model. Required is accurate phenotyping of the members of a test population or germplasm panel and the high-density genotyping ($10^4$-$10^5$ markers) of the same individual. From these two data types, a model is constructed by one of the multiple methods available to this in the public domain [e.g. Meuwissen et al, 2001]. Optionally, the prediction quality of the constructed model is tested on a second population from which both genotypes and phenotypes have been measured.

Selection Phase

In the second phase, all members of a breeding population are genotyped, using the same marker set of the training phase. By entering the genotypic data in the model constructed in the previous phase, breeding values are predicted for each individual without doing any actual phenotypic measurement. Selections are made from populations for breeding purposes, based on the predicted values.

However, the optimal strategy of selecting individuals to obtain the best gain in phenotype improvement has not been worked out in the prior art. Therefore, it is an object of the present invention to provide for an improved procedure which is better optimized, as compared to the prior art, to identify (and select) the individuals that have the highest probability to produce the best performing offspring in the next generation.

SUMMARY OF THE INVENTION

The present inventors came to the realization that the prior art selection strategy does not consider the long-term impact on the breeding process of the selection made in the current population. This is because in prior art methods, the best per se performing parents will be selected, assuming that, under an additive model, crossing these will result in the best performing genotypes in the next generations.

However, if, for example, two parents are selected from which the favorable alleles are largely overlapping, the future improvement of the genotype will be limited to obtaining fixed homozygous allele states for these loci (a state that may also be reached by inbreeding from a single parent), and missing the selection opportunity to gather additional favorable alleles on alternative loci by introduction via other parents.

The prior art methodology to make selections in breeding based on or predicted by a GS model is shaped after the practice of traditional selection on phenotypic observations and is overlooking that a genomic prediction model contains detailed information about which genome sections are most contributing to the positive and negative performance of the trait. Although the basic principle of GS is the assumption that all loci of a genome contribute to the trait, most GS models specify only an additive effect for each single locus (see e.g. EP1962212, or US2010/0037342). Therefore, although both a directly measurable phenotype and a given GS prediction model might predict an equally high quantitative trait value for two arbitrary individuals, for the next breeding step, it makes a large difference whether in both cases the superior performance is predicted by identical loci in both genomes or by different genomic regions. In the latter case, improvement of the trait average may be expected in the next breeding cycles, by combining the favorable alleles, whereas in the first case it may not.

In phenotypic as well as genomic selection, the performance of the parents does not adequately predict their mutually combined ability and expected success of the resulting genotype of the crosses to be made in the next generation or generations.

A first attempt to predict the combined ability and expected success of different parent pairs is described in WO2012075125. Briefly, the document suggests to calculate breeding values of different parent pairs by taking the mean breeding value of simulated offspring genotypes of each parent pair. However, the present inventors recognized that the full potential of a population, e.g. with respect to a certain trait, lies in the combination of multiple parents, i.e. more than a single parent pair), because complete genomewide complementarity is unlikely to occur within a single parent pair. Indeed, in several experiments the present inventors discovered a strongly enhanced efficiency of a genomic selection strategy that is based on the selection of a subset of at least 3 parents as compared to strategies that are based on the selection of single parent pairs (regular genomic selection) and crossing of said pairs.

Technically, the present inventors achieved this by focusing on Genomewide Estimated Breeding Values from the genotypes of the combination of at least 3 individuals of the parent generation, rather than by focusing on the genotype of individual pairs. Each subset of at least 3 marker genotypes can be considered as a library of haplotypes, from which multiple combinations have a predictable likelihood to produce genotypes with the predicted highest achievable phenotypic value. In some embodiments, this will be reached by recombination of the existing haplotypes within a genotype prior to transmission to the offspring in the next breeding cycle or plurality of breeding cycles. Of course, genotypes can only be recombined by crossing of two parents or self-fertilization. However, as will be clear to the skilled person, mixing of subsets of at least 3 genomes can be achieved via several parallel and/or subsequent crosses, which can be performed after the selection method according to the present disclosure.

The present disclosure thus extends the use of the GS model as developed in the training phase (in which no changes are proposed) by improving the efficiency in the selection phase. This procedure enables the selection of groups of at least 3 individuals that have the highest probability to produce the best performing offspring in the next generations, rather than to select the best performing pairs. This approach was shown to achieve unexpectedly better breeding results in simulation models.

As an example of the principle underlying the present disclosure, FIG. 1 shows a graphical representation of the selection process in a breeding population consisting of 3 diploid individuals represented by their genotypes G1-3. The individuals have been genotyped for 5 loci L1-5 and the phenotype for an individual with a particular genotype can be predicted using a mathematical genome-wide prediction model that assigns positive or negative effects to each allele occurring on the loci. The concept of the current disclosure involves the construction of the putative future genotype that predicts the highest phenotypic performance from haplotypes (H1.1-H3.2) occurring in the current population, or recombinants of those. In the example of FIG. 1, the best obtainable genotype that can be obtained with a single cross is combining haplotypes H1.1 and H3.1 (indicated bold), which complement each other in locus L5 versus the others. According to the present disclosure, and extrapolating from FIG. 1, it will be clear that in larger populations, the putative genotype can be constructed analogously from haplotypes of more than two individuals.

In case recombination between loci with another haplotype would lead to an increase of positively contributing alleles (as in haplotype H 1.1) the breeding value is calculated from the recombinant haplotype, multiplied with the probability that this recombination occurs between the loci (example $P[\theta_{1 \to 2}]$ with $\theta_{1 \to 2}$ defining the estimated frequency of recombination between locus 1 and 2). On the other hand, if recombination would lead to a decrease of positively contributing alleles, the predicted phenotype value of the haplotype is multiplied with the probability of no recombination occurring (example $P[\text{not } \theta_{3 \to 4}] = 1 - P[\theta_{3 \to 4}]$).

Another example is shown in Table 1 which shows a selection strategy from a population using Combined Genomic Estimated Breeding Values. From a very small population of 5 diploid homozygous individuals the genotypes have been established (represented by 12 loci; top side of the table). If each allele marked "A" is positively contributing to a desired trait value, according to a genomic prediction model and "B" indicates all other alleles, the best achievable genotype contains the highest fraction of "A" alleles.

The genomic estimated breeding values (GEBVs) of each individual are shown in the boxed cells on the diagonal of the lower part of the table, the off-diagonal cells contain CGEBVs.

Following the prior art selection procedure using GEBVs, the individuals with the highest values would have been selected as parents for the next generation, which are in the example of Table 1 individuals 1, 2 and 4. However, when taking the combined ability of parent pairs into account, the result may be different. For example in Table 1, when ranking the Combined GEBVs, it becomes apparent that the combinations of individuals 1 and 2; 1 and 3; as well as 1 and 5 are superior over 1 and 4, as these parent pairs have a better prospective for the production of the highest ranking genotypes in the next generation.

The prospect of finding the best allele gathering in the described population becomes even better when combinations of more than two parents are compared. When all combinations of three parents are compared, it becomes apparent that the combinations (1, 2 and 3) and (1, 2 and 5) are the superior triplets with a CGEBV of 0.92 (not shown in the table), while the triplet of superior per se GEBV parents (1, 2 and 4) have a CGEBV of only 0.83. The superior triplets cannot directly be inferred from the superior CGEBVs as calculated for the two-parent combinations, which are (1, 2), (1, 3) and (1, 5). In the example of Table 1, this becomes clear because the combination (1, 3 and 5) has a lower CGEBV (0.83) than the combinations (1, 2 and 5) and (1, 2 and 3), which can only be found if the three-parent combinations are compared.

Since all individuals in the example of Table 1 are homozygous, for pairwise (first generation) CGEBV estimation, recombination processes are irrelevant.

values, individual 1 and 2 are the top ranking parents (0.33 and 0.21, respectively), but the CGEBV ranking for the different parent pairs shows that actually the combinations (1, 3), (1, 4) and (1, 5) are able to produce the best offspring genotypes. The genotypes of individual 3, 4 and 5 are identical, however the allele phases of the haplotypes differ. The alleles of the first haplotype of individual 3 includes all favorable alleles in linkage phase and requires no recombination event to pass on all favorable alleles to the offspring. In the genotypes of individuals 4 and 5, two recombinations are required to transmit all alleles in a single haplotype. In individual 4, the first of the required recombinations is between loci 2 and 4, while in individual 5 this is between loci 1 and 2. If the genetic distance between loci 2 and 5 is larger, the required recombination events are more probable to occur in individual 4. By correcting the initial CGEBV value in the table with the probability of the recombination events occurring, the CGEBV ranking of individual 1 with the others will become 3, 4, 5, 2. As a result, the combination of individual 1 and 3 is the best parent pair for the next generation in the current panel.

TABLE 1

|            | Loci 1 | Loci 2 | Loci 3 | Loci 4 | Loci 5 | Loci 6 | Loci 7 | Loci 8 | Loci 9 | Loci 10 | Loci 11 | Loci 12 |
|---|---|---|---|---|---|---|---|---|---|---|---|---|
| Genotype 1 | A | A | A | B | B | B | A | A | B | B | A | A |
|            | A | A | A | B | B | B | A | A | B | B | A | A |
| Genotype 2 | B | B | A | A | B | A | A | A | B | B | B | B |
|            | B | B | A | A | B | A | A | A | B | B | B | B |
| Genotype 3 | A | B | B | B | A | B | B | B | A | B | B | B |
|            | A | B | B | B | A | B | B | B | A | B | B | B |
| Genotype 4 | B | A | A | B | B | B | A | A | A | B | B | B |
|            | B | A | A | B | B | B | A | A | A | B | B | B |
| Genotype 5 | B | B | B | B | A | B | B | B | B | A | B | B |
|            | B | B | B | B | A | B | B | B | B | A | B | B |

Combined Genomic Estimated Breeding Values (CGEBVs)

|            | Genotype 1  | Genotype 2  | Genotype 3  | Genotype 4  | Genotype 5  |
|---|---|---|---|---|---|
| Genotype 1 | 0.583333333 | 0.75        | 0.75        | 0.666666667 | 0.75        |
| Genotype 2 |             | 0.416666667 | 0.666666667 | 0.583333333 | 0.583333333 |
| Genotype 3 |             |             | 0.25        | 0.583333333 | 0.333333333 |
| Genotype 4 |             |             |             | 0.416666667 | 0.583333333 |
| Genotype 5 |             |             |             |             | 0.166666667 |

A further example is shown in Table 2 which shows a selection strategy as in Table 1, but now applied to a heterozygous population and taking recombination events into account. In the example of Table 2, according to GEBV

TABLE 2

|            | Loci 1 | Loci 2 | Loci 3 | Loci 4 | Loci 5 | Loci 6 | Loci 7 | Loci 8 | Loci 9 | Loci 10 | Loci 11 | Loci 12 |
|---|---|---|---|---|---|---|---|---|---|---|---|---|
| Genotype 1 | A | A | A | A | B | B | B | B | B | B | B | B |
|            | B | B | B | B | B | A | A | B | B | B | A | A |
| Genotype 2 | B | B | B | B | B | B | A | A | A | B | B | B |
|            | B | A | A | B | B | B | B | B | B | B | B | B |
| Genotype 3 | A | A | B | B | A | B | B | B | A | B | B | B |
|            | B | B | B | B | B | B | B | B | B | B | B | B |
| Genotype 4 | A | A | B | B | B | B | B | A | B | B | B | B |
|            | B | B | B | B | A | B | B | B | B | B | B | B |
| Genotype 5 | A | B | B | B | B | B | B | A | B | B | B | B |
|            | B | A | B | B | A | B | B | B | B | B | B | B |

Genomic Estimated Breeding Values (CGEBVs)

|            | Genotype 1 | Genotype 2 | Genotype 3 | Genotype 4 | Genotype 5 |
|---|---|---|---|---|---|
| Genotype 1 | 0.333333   | 0.75       | 0.833333   | 0.833333   | 0.833333   |
| Genotype 2 |            | 0.208333   | 0.583333   | 0.583333   | 0.583333   |

TABLE 2-continued

| Genotype 3 | 0.166667 | 0.333333 | 0.333333 |
| Genotype 4 | | 0.166667 | 0.333333 |
| Genotype 5 | | | 0.166667 |

Definitions

In the following description and examples, a number of terms are used. In order to provide a clear and consistent understanding of the description and claims, including the scope to be given such terms, the following definitions are provided for the terms as used in the description and claims. Unless otherwise defined herein, all technical and scientific terms used have the same meaning as commonly understood by one of ordinary skill in the art to which this invention belongs.

Selection and selection criteria: process, model, system or algorithm in order to choose individuals in a population that will contribute genetic material to the next generation. In particular, such a process, model, system or algorithm can be based both on natural or artificial phenomena or procedural steps. Selection criteria can be based on phenotypic or genomic characteristics, for instance, but not limited to, the presence, or degree of presence, of genes, gene expression, genetic markers, combinations of genes, quantitative trait loci, traits or combinations of traits.

Breeding value: the genetic merit of a unit of inheritance such as an individual in a breeding program. This genetic merit is determined by the contribution to at least one phenotypic trait of interest of an individual's gene or genes or (genetic) loci in a breeding program aimed at improving the at least one phenotypic trait of interest.

Estimated breeding value: an approximation of an individual's breeding value, in particular based on the estimated difference between the average performance of that individual's offspring and the average performance of all offspring in a randomly mating population. The estimated average performance of all offspring in a randomly mating population may take into account that individuals with inter-familial relationships, i.e. pedigree relations, normally do not mate.

Genome-wide estimated breeding value: estimated breeding value based on genome-wide information, i.e. information derived from different or remote (genetic) loci of the genome such as loci of different chromosomes. In particular, genome-wide estimated breeding values are an approximation of an individual's genome-wide genetic merit, determined by the contribution to at least one phenotypic trait of interest of an individual's genome-wide genes or genome-wide (genetic) loci, or genome-wide haplotypes or genome-wide molecular marker scores in a breeding program aimed at improving the at least one phenotypic trait of interest.

Combined Genome-wide Estimated Breeding Value (CGEBV): Genome-wide Estimated Breeding Value of a combination of three or more individuals within a population. The combination with the highest CGEBV (as compared to the other combinations) together have the highest estimated probability to produce the best performing offspring in subsequent generations in a breeding program aimed at improving an at least one phenotypic trait of interest. So, the CGEBV actually accounts for the genome-wide estimated breeding values of the genotypes of the putative offspring, and does not solely consider the genotype of each individual potential parent separately. In particular, the potential parents may not be the best performing individuals per se, or the potential parents with the best genome-wide estimated genomic breeding value.

Directed genome-wide selection: selection method based on focusing on a combination of individuals in a population that together have the highest probability to produce the best performing offspring in the next generations in a breeding program aimed at one or more selection criteria. With directed genome-wide selection the focus is on genome-wide estimated breeding values of the genotypes of the putative offspring (combined genome-wide estimated breeding value), rather than by focusing on the genotype of each individual parent itself. In particular, this selection method is not based on selecting the best performing individuals per se.

Regular genome-wide selection: selection method based on crossing parents with the best genome-wide estimated breeding values per se.

Offspring: as used herein, the term "offspring", refers to the first or further generation obtained by intercrossing.

Phenotype: the composite of an individual's characteristics or traits, particularly observable characteristics or traits, such as, but not limited to morphological, physical, biochemical, developmental or behavioral characteristics or traits. The phenotype of an individual can be formed by the expression of genes as well as environmental factors, and on interactions between gene expression and environmental factors.

Phenotypic trait of interest: a heritable characteristic of a plant or animal species which may be quantified in a certain unit of measure. Examples of quantitative phenotypic traits of interest are (but are not limited to) for plants: fruit size, fruit count, yield in kg per ha, plant height, relative growth speed, flowering time, germination rate, leave area, disease resistances, yield components, biochemical composition, and for animals: milk yield, milk protein content, carcass weight, fodder conversion, body fat composition, litter size, coat color, resistances to diseases. It can be desired that a quantitative phenotypic trait of interest is increased or decreased, and the respective shift of the average value for the characteristic in the population can improve the economic value of that population, variety or offspring relative to the parent generation(s).

Genotype: as used herein, the term "genotype" refers to the genetic makeup of a cell, an organism, or an individual (i.e. the specific allele makeup of the individual) usually with reference to a specific character or phenotypic trait of interest under consideration. However, not all organisms with the same genotype necessarily look or act the same way because appearance and behavior are modified by environmental and developmental conditions. Likewise, not all organisms that look alike necessarily have the same genotype.

Genotyping: as used herein, the term "genotyping" or "determining the genotype" refers to the process of determining genetic variations among individuals in a species. Single nucleotide polymorphisms (SNPs) are the most common type of genetic variation that are used for genotyping and by definition are single-base differences at a specific locus that is found in more than 1% of the population. SNPs are found in both coding and non-coding regions of the genome and can be associated with a phenotypic trait of interest such as a quantitative phenotypic trait of interest. Hence, SNPs can be used as markers for quantitative phenotypic traits of interest. Another common type of genetic variation that are used for genotyping are "InDels" or insertions and deletions of nucleotides of varying length. For both SNP and InDel genotyping, many methods exist to determine genotype among individuals. The chosen method generally depends on the throughput needed, which is a function of both the number of individuals being genotyped and the number of genotypes being tested for each individual. The chosen method also depends on the amount of sample material available from each individual or sample. For example, sequencing may be used for determining presence or absence of markers such as SNPs, e.g. such as Sanger sequencing and High Throughput Sequencing technologies (HTS). Sanger sequencing may involve sequencing via detection through (capillary) electrophoresis, in which up to 384 capillaries may be sequence analysed in one run. High throughput sequencing involves the parallel sequencing of thousands or millions or more sequences at once. HTS can be defined as Next Generation sequencing, i.e. techniques based on solid phase pyrosequencing or as Next-Next Generation sequencing based on single nucleotide real time sequencing (SMRT). HTS technologies are available such as offered by Roche, Illumina and Applied Biosystems (Life Technologies). Further high throughput sequencing technologies are described by and/or available from Helicos, Pacific Biosciences, Complete Genomics, Ion Torrent Systems, Oxford Nanopore Technologies, Nabsys, ZS Genetics, GnuBio. Each of these sequencing technologies have their own way of preparing samples prior to the actual sequencing step. These steps may be included in the high throughput sequencing method. In certain cases, steps that are particular for the sequencing step may be integrated in the sample preparation protocol prior to the actual sequencing step for reasons of efficiency or economy. For instance, adapters that are ligated to fragments may contain sections that can be used in subsequent sequencing steps (so-called sequencing adapters). Primers that are used to amplify a subset of fragments prior to sequencing may contain parts within their sequence that introduce sections that can later be used in the sequencing step, for instance by introducing through an amplification step a sequencing adapter or a capturing moiety in an amplicon that can be used in a subsequent sequencing step. Depending also on the sequencing technology used, amplification steps may be omitted.

Genotype/phenotype relationship model: a model that can associate (correlate) genotype with phenotype for individuals in a population. To create such model it is typically required to phenotype individuals of a population and genotype the same individuals. In particular, genotyping can be based on high-density marker data, such as data on the presence or absence of a SNP at a plurality of loci. Likewise, phenotyping can be performed at high accuracy, for example by measuring the value for the quantitative phenotypic trait of interest per individual. The genotype/phenotype relationship model can then be created by calculating correlations between the genotypic data and the phenotypic data. For example, with a dense marker map, such as SNP map, some markers can be correlated with positive or negative effects on a particular quantitative phenotypic trait of interest. In this way, the model can attribute a contribution to the quantitative phenotypic trait of interest to the presence or absence of a marker. Said contribution may for example be expressed in kg, m, L, depending on the unit of measure as used for the quantitative phenotypic trait of interest (for example fruit size, milk production, etc.). Various methods are available in the art in order to construct such a model (Meuwissen et al., 2001).

Locus: as used herein, the term "locus" or "loci" (plural) refers to a specific site (place) or sites on the genome. For example, the "locus" refers to the site in the genome where the two alleles of the locus are found (for diploid organisms). Quantitative trait loci (QTLs) are sites on the genome containing alleles that are associated to a quantitative trait (based on the genotype/phenotype relationship model).

Allele: the term "allele" refers to the nucleotide sequence variant that is present on one of the positions of a particular locus. A diploid individual has two positions for one allele per locus, one position on either one of the two homologous chromosomes. For each of the positions of a particular locus, one or more alternative nucleotide sequence variants may exist in a population, i.e. for each position different possible alleles may exist in a population. However, each individual can have only one of the possible alleles on each one of the positions of a locus. The alternative nucleotide sequence variants, i.e. the different possible alleles, differ at least slightly in nucleotide sequence, and typically can be distinguished based on the presence or absence of at least one SNP or InDel. When referred herein to an "allelic state", reference is made to the presence or absence of an allele at a position within a particular locus, which can be expressed as the presence or absence of the respective marker (e.g. SNP or indel) at the particular locus.

Allele dose of a locus: the number of copies present in a genome of a given allele on a given locus. The range for the allele dose is between 0 (no copies present) to the (auto) ploidy level of the genome; i.e. for diploid species, the allele dose for a given allele can be either 0, 1 or 2. For polyploid genomes the max allele dose corresponds to the number of homologous chromosome copies.

Attributed Allele substitution effect: this term refers to the estimated quantitative effect on the trait when on a given locus the one allele (e.g. as measured by presence of a particular SNP) is substituted by the other allele (e.g. as measured by absence of the particular SNP) within a given genetic and/or environmental background. For example, if fruit yield is the quantitative phenotypic trait of interest in a population of plants, the quantitative effect on that trait may be expressed in kg. Based on the genotype/phenotype relationship model, a particular allele on a given locus (e.g. as measured by presence of a particular SNP) can thus be attributed an allele substitution effect of e.g. 0.0001 kg, which means that if the particular allele is replaced by the other possible allele (e.g. as measured by absence of the particular SNP), the quantitative effect on the trait, i.e. fruit yield is estimated to be 0.0001 kg.

Attributed Allele substitution effect corrected for recombination probability: Attributed allele substitution effects can be corrected for recombination probabilities. The further away two loci are from each other, the more likely it is that recombination (crossing over) takes place between the two loci. The distance between loci is measured in terms of recombination probability and is given in cM (centiMorgans; 1 cM is a meiotic recombination probability between two markers of 1%). This is relevant because for both positively and negatively contributing alleles, one would like to know the chance that they are transmitted to offspring. A positive attributed allele substitution effect can be corrected for recombination probability by taking into account the probability that (after crossing with another individual) the allele is transmitted to the genome of offspring. A negative attributed allele substitution effect can be corrected for recombination probability by taking into account the probability that (after crossing with another individual) the allele is not transmitted to the genome of offspring.

Heterozygous and homozygous: as used herein, the term "heterozygous" refers to a genetic condition existing when two different alleles reside at a specific locus, for example a locus having alleles A/B, wherein A and B are positioned individually on either one of the two homologous chromosomes. Conversely, as used herein, the term "homozygous" refers to a genetic condition existing when two identical alleles reside at a specific locus, for example a locus having alleles A/A, positioned individually on either one of the two homologous chromosomes.

Molecular marker technique: as used herein, the term "molecular maker technique" refers to a (DNA based) assay that indicates (directly or indirectly) the presence or absence of a marker allele of interest in an individual (e.g. (crop) plant or cattle). Preferably, it allows one to determine, e.g. by sequencing, whether a particular allele is present or absent at one of the positions at the locus in any individual.

DETAILED DESCRIPTION OF THE INVENTION

The present disclosure relates to a method for selecting combination(s) of at least three individuals within a breeding population, wherein the combinations have, for at least one phenotypic trait of interest, a higher Combined Genome-Wide Estimated Breeding Value in the offspring for said at least one phenotypic trait of interest, as compared to at least 70% of the other combinations of at least three individuals within said breeding population. The present method comprises the following steps:

a) providing a training population of individuals;
b) collecting phenotypic data for the at least one trait of interest for each individual within said training population;
c) collecting genotypic data for each individual within said training population using molecular marker techniques, sequence-based genotyping or whole genome sequencing, and attributing to each allele of a plurality of loci of each individual, an allele substitution effect for the at least one phenotypic trait of interest;
d) providing a genotype/phenotype relationship model for said training population of individuals, wherein the model estimates for a given genotype of an individual what the quantitative contribution is of the allele substitution effects of said plurality of loci on the at least one phenotypic trait of interest;
e) genotyping each individual within a breeding population, preferably (by collecting genotypic data for each individual within said breeding population) in the same way as in step c);
f) calculating for each individual within the breeding population the allele substitution effect for each allele of said plurality of loci by using the genotype/phenotype relationship model of step d), and correcting for recombination probabilities with flanking loci, wherein for an allele with a positive allele substitution effect said effect is multiplied with the probability that said allele is transmitted to the offspring, and for an allele with a negative allele substitution effect said effect is multiplied with the probability that said allele is not transmitted to the offspring;
g) determining the Combined Genome-Wide Estimated Breeding Value in the offspring for the at least one phenotypic trait of interest for each combination of at least three individuals within the breeding population by calculating for each combination of at least three individuals for each locus of said plurality of loci in the offspring the highest combination of allele substitution effects using the calculated and corrected allele substitution effects of the individuals calculated in step f);
h) identifying the combinations of at least three individuals within the breeding population that provide for said at least one phenotypic trait of interest Combined Genome-Wide Estimated Breeding Values in the offspring that are higher than at least 70% of the Combined Genome-Wide Estimated Breeding Values in the offspring of other combinations of individuals within the breeding population.

While previous methods focus on identifying the (pairs of) individuals within the breeding population that on their own have the best genome-wide estimated breeding values, the present method allows to identify which subset(s) of at least three parents together have the best combined genome-wide estimated breeding value. In this way, one could say that the present method actually assesses the genome-wide estimated breeding value of the putative offspring of different combinations of at least three potential parents.

In other words, the method allows to identify (and/or (subsequently) select) at least one (e.g. at least 2, at least 3, at least 5, or at least 10) combination of at least three (e.g. at least 5, at least 10) individuals in a (breeding) population that together have the highest probability to produce the best performing offspring in the next generation(s) in a breeding program aimed at improving at least one (or at least 2, 3, 4) (quantitative) phenotypic trait of interest. Where reference is made to a CGEBV in the offspring of a combination, the CGEBV of the respective combination of individuals is meant which reflects the breeding value of their putative offspring.

For example, in a population of four individuals a, b, c, d three possible combinations are: (a, b, and c); (a, c, and d); (b, c and d). If in this example the combination (a, b, and c) has a CGEBV of 10, the combination of (a, c, and d) has a CGEBV of 20, and the combination (b, c and d) has a CGEBV of 30, the method can identify the combination (b, c and d) as the best combination of three individuals (subset). However, the method also allows to identify and/or select more than one combination for use in a subsequent breeding program, e.g. in this example the method can identify the combination (b, c and d) as well as the combination (a, c, and d), because their CGEBVs are both higher than that of the combination (a, b, and c). Exactly the same principle can be applied to extract subgroups of more than three parents out of larger panels, by calculating CGEBVs for all triplets, quartettes etc. and ranking these.

In step a) of the method, a (training) population of individuals is provided. This population can optionally be called a training population, because it serves for the establishment of a genotype/phenotype relationship model. Such model allows to attribute an allele substitution effect on the at least one phenotypic trait of interest to each of the alleles of a plurality of loci of individuals of a breeding population. Therefore, preferably, the training population and the breeding population relate to the same plant or non-human animal species, and more preferably the training population is the same as the breeding population or most preferably a selection of individuals therefrom. It is also possible that the training population is a specifically designed population, which means that the population is specifically compiled for the purpose of generating a phenotype/genotype relationship model.

In the present disclosure, the term "individual" refers to living subjects, and in particular to (crop) plants or non-human animals such as cattle. Preferably the training population comprises at least 3, at least 10, or at least 50 individuals, but (in particular if the individuals are plants) the training population may also comprise at least 100, or at least 500 individuals.

In step b) of the method, phenotypic data is collected for the at least one phenotypic trait of interest for each individual within said population. For example, if the trait concerns the quantity of milk production (cattle), or the size of the flowers (plants), one can measure, for each individual of the training population, the quantity of milk production (in L) or the size of the flowers (diameter in m).

Then step c) of the method collects genotypic data for each individual with the training population using methods well-known to the skilled person, such as molecular marker techniques, sequence-based genotyping or whole genome sequencing. As explained earlier herein, genotyping, or determining the genotype refers to the process of determining genetic variations among individuals in the population. For this, the skilled person has various molecular biology techniques at his disposal such as hybridisation analysis, PCR and preferably sequencing in order to examine DNA molecules of the individuals in order to unravel sequence variations between said individuals.

The molecular marker technique(s) used in the present method are preferably selected from the group consisting of the detection of SNPs, the detection of RFLPs, the detection of SSR polymorphisms, RAPDs, the detection of indels or CNVs, and AFLP.

Molecular biology techniques are well-known to the skilled person and for example described in standard handbooks such as Sambrook and Russell (2001) Molecular Cloning: A Laboratory Manual, Third Edition, Cold Spring Harbor Laboratory Press, NY; and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, published by BIOS Scientific Publications Ltd (UK) and Blackwell Scientific Publications, UK.

Step c) then continues with attributing to each allele of a plurality of loci of each individual, an allele substitution effect for the at least one phenotypic trait of interest. Said attributing is typically based on the identification of correlations between the phenotypic data and the genotypic data. In this respect, the term "allele substitution effect", as also explained elsewhere herein, refers to an estimated quantitative effect on a certain phenotypic trait when on a given locus the one allele (e.g. as measured by presence/absence of a particular SNP) is substituted by the respective allele (e.g. as measured by presence/absence of the particular SNP) within a given genetic and/or environmental background.

For example, the allele substitution effect of a certain allele with SNP versus an allele without the SNP on the same position can be based on comparing phenotypes of individuals having only the allele with SNP with phenotypes of individuals having only the allele without SNP. Such comparing may identify correlations between the genotype and the phenotype.

After steps a), b), and c), step d) can provide a genotype/phenotype relationship model for the training population of individuals, wherein the model allows to estimate (and/or attribute) for a given genotype of an individual within a breeding population, what the quantitative contribution is of the allele substitution effects of the plurality of loci on the at least one phenotypic trait of interest. In other words, the model can attribute to each allele of the plurality of loci, an allele substitution effect based on the correlations found while or after producing the genotype/phenotype relationship model.

If the present method uses a preexisting (or prior prepared) genotype/phenotype relationship model for the individuals of the breeding population, steps a), b), c), and d) are not required (and thus optional).

In step e), each individual within a breeding population is genotyped, for which molecular marker techniques well-known to the skilled person can be used. The molecular marker technique(s) used in the present method are preferably selected from the group consisting of the detection of SNPs, the detection of RFLPs (differing locations of restriction enzyme sites), the detection of SSR (Simple Sequence Repeat) polymorphisms, RAPDs (Random Amplification of Polymorphic DNA), the detection of indels or CNVs (Copy Number Variations), and AFLP (Amplified Fragment Length Polymorphism).

In step f) of the present method, for each individual within the breeding population, for each allele of a (the) plurality of loci, the allele substitution effect is calculated (attributed) using the genotype/phenotype relationship model of step d). In this respect, the breeding population refers to the population of individuals which can be further intercrossed with the aim of improving the at least one phenotypic trait in subsequent generation(s). So, within step e) (or prior to step e)) the providing of a breeding population is envisaged. It will be clear that the attribution of allele substitution effects to the individuals within the breeding population can be based on the results of prior genotyping of said individuals.

In the context of the present method, the plurality of loci may refer to as few as two, five, or twenty loci which may be located on separate regions of the genome such as different chromosomes, but the term plurality may also refer to at least 10, at least 25, at least 100, or at least 500, or at least 1000, or at least 5000 or more different loci preferably located on separate regions of the genome such as different chromosomes.

In a preferred embodiment of the present method, the plurality of loci are (genome-wide) loci located on the entire genome, e.g. located on at least 2, at least 5, at least 10, or at least 20 chromosomes. At the same time or alternatively, the plurality of loci comprises at least 100, at least 500, at least 1000, or at least 2000 loci. Furthermore, it is preferred that at least one loci of the plurality of loci is found every 100 cM, preferably every 50 cM, more preferably every 25 cM, even more preferably every 10 cM, even more preferably every 5 cM, most preferably every 1 cM of the genome.

Step f) also aims to correct the attributed allele substitution effects as awarded to each allele of the plurality of loci, for (estimated) recombination probabilities with flanking loci (e.g. the previous or preferably the next loci (or both) in the 5' to 3' direction). This is done by correcting each allele of the plurality of loci that is attributed a positive allele substitution effect for the (estimated) recombination probability that (after crossing with another individual) the allele is transmitted to the genome of offspring, and, correcting each allele of the plurality of loci that is attributed a negative allele substitution effect for the (estimated) recombination probability that (after crossing with another individual) the allele is not transmitted to the genome of the offspring. In this way, step f) of the method allows for correcting of the attributed allele substitution effects attributed to each allele of the plurality of loci of each individual within the population for (estimated) recombination probabilities.

Correction of a positive attributed allele substitution effect is preferably (not necessarily) done by multiplying the effect with the probability that the corresponding allele is transmitted to the offspring (i.e. a gamete), and correction of a negative attributed allele substitution effect is preferably (not necessarily) done by multiplying the effect with the probability that the corresponding allele is not transmitted to the offspring (i.e. a gamete).

In a preferred embodiment of step f) of the method, the recombination probabilities are calculated based on genetic distances between loci, or based on aligning physical and genetic maps. Further details hereon may be found in Liu (1998).

The present method then continues with step g) relating to determining the Combined Genome-wide Estimated Breeding Value (in the offspring) for the at least one phenotypic trait of interest for each combination of at least three individuals within the (breeding) population by calculating for each combination of at least three individuals for each locus of said plurality of loci (in the offspring) the highest combination of allele substitution effects using the calculated and corrected allele substitution effects of the individuals calculated in step f).

So, the present method takes into account, for each attributed allele substitution effect, the chance that the corresponding allele actually ends up in a gamete of an individual. This is relevant because for both positively and negatively contributing alleles, one would like to know the probability that they are transmitted to a gamete. For example, one could consider the following plurality of loci consisting of three loci of individual 1:

| Individual 1 | | |
|---|---|---|
| Locus 1 | 1 | 0 |
| Locus 2 | 1 | 0 |
| Locus 3 | 0 | 1 |

(wherein 1 refers to presence of the marker allele and 0 to the absence of the marker allele)

Based on a genotype/phenotype relationship model, the following allele substitution effects may have been attributed to the alleles of the loci:

| Locus 1 | 0.1 | 0 |
|---|---|---|
| Locus 2 | −0.2 | 0 |
| Locus 3 | 0 | 0.15 |

As can be seen, recombination between locus 1 and locus 2 is desired such that the first allele of Locus 1 and the second allele of Locus 2 are transmitted to a gamete, because this leads to an increase in attributed allele substitution effects in the gamete. On the other hand, recombination between the second allele of Locus 2 and the first allele of Locus 3 is not desired, because that would lead to a decrease of attributed allele substitution effects in the gamete.

Based on methods well-known to the skilled person, such as methods disclosed in Liu (1998), the probability that recombination occurs between two loci can be calculated based on the genetic distance between the two loci. This calculation is based on the fact that the chance of recombination occurring between loci that are located proximal to each other is lower as compared to the chance of recombination occurring between loci that are located less proximal to each other. In this example, the following estimated recombination probabilities may have been estimated:

| | Probability of recombination occurring with the previous locus: | Probability of no recombination occurring with the previous locus: |
|---|---|---|
| Locus 1 | 1 | 0 |
| Locus 2 | 0.1 | 0.9 |
| Locus 3 | 0.15 | 0.85 |

So, in this example, the positive allele substitution effect attributed the first allele of locus 1 now should be corrected for the probability that this allele is transmitted to a gamete, and the negative attributed allele substitution effect of the first allele of locus 2 should be corrected for the probability that the allele is not transmitted to a gamete. Finally, the positive attributed allele substitution effect of the second allele of locus 3 should be corrected for the probability that this allele is transmitted to a gamete:

| | Corrected attributed allele substitution effect |
|---|---|
| Locus 1 | 0.1 × 1 = 0.1 |
| Locus 2 | −0.2 × 0.1 = −0.02 |
| Locus 3 | 0.15 × 0.85 = 0.1275 |

The total of corrected allele substitution effects for loci 1-3 of this individual thus is 0.1+(−0.02)+0.1275=0.2075.

Then, the Combined Genome-wide Estimated Breeding Value (CGEBV) of a combination of two individuals is calculated by taking for each locus of the plurality of loci, the highest corrected locus effect S (corrected allele substitution effects of the locus) of the individuals of the combination.

Then, step h) selects the at least one combination(s) of at least three individuals within the (breeding) population that have a higher CGEBV (preferably the highest) for the at least one phenotypic trait of interest, as compared to at least 70% of the other combinations, preferably as compared to at least 80%, 90%, 95%, 99% or most preferably 100% of the other combinations of at least three individuals within the breeding population.

In a preferred embodiment, the present method allows for a pre selection of individuals within the breeding population. This pre selection preferably takes place after the providing of the breeding population in step e) of the method. The pre selection allows to reduce the number of individuals to be considered for the calculating part of step e), and thus allows to reduce the number of combinations of individuals for which the CGEBV has to be calculated. In practice this may be worthwhile in certain situations, particularly when the number of individuals or combinations of individuals, or the number of loci to be considered demands more computational power than the user of the method can provide. In such scenario, it may be advantageous to perform a pre selection to reduce the number of (combinations of) individuals for which the CGEBV has to be calculated.

Preferably, the pre selection of individuals within the breeding population to be combined is made by selecting (exclusively) at most 30%, more preferably at most 20%, even more preferably at most 10%, yet even more preferably at most 5%, most preferably at most 2% of the individuals with the highest sum (or higher as compared to the other, not selected individuals) of all corrected allele substitution effects attributed to the plurality of loci.

So, for the optional pre selection, first, the corrected attributed allele substitution effect of each locus of each individual in the population can be calculated. In this respect, said corrected attributed allele substitution effect of a particular locus can be referred to as the "corrected locus effect" of that particular locus. The result of calculating the corrected locus effects of a (sub set of the) plurality of loci shows which individuals have higher corrected locus effects for certain subsets of the plurality of loci than the other individuals, which can form the basis of a pre selection. For example, one can identify which individuals have higher corrected locus effects for different parts of the plurality of loci, e.g. relating to parts of the plurality of loci associated with at most part of the genome, e.g. one chromosome. For example, if the plurality of loci comprises 100 loci, one can make a pre selection of e.g. five individuals, being the individual with the highest total of locus effects for loci 1-20, the individual with the highest total of locus effects for loci 21-40, the individual with the highest total of locus effects for loci 41-60, the individual with the highest total of locus effects for loci 61-80, and the individual with the highest total of locus effects for loci 81-100.

The pre selection can for example be performed by selecting individuals with a higher value for S for part of the plurality of loci, e.g. a plurality of loci of at least part (or at most part) of the genome, such as only the loci located on one chromosome, as compared to the value S as determined for the same part of the plurality of loci of the other individuals, wherein S=PF wherein P∈$R^{n\times p}$, and F∈$R^{p\times p}$, wherein R is a set of real numbers (excluding imaginary numbers), n is the number of parents, p is the number of loci that is considered. In other words, S represents the corrected locus effect of a particular locus, i.e the sum of corrected attributed allele substitution effect of that locus. S can be calculated by multiplying P and F, wherein P represents the (uncorrected) locus effect of a particular locus, and F represents the estimated recombination probability between flanking loci.

Subsequently, one way of performing step g) of the present method is by calculating CGEBV according to Formula I:

$$CGEBV = c_{\vartheta_1, \vartheta_2} = \sum_{i=1}^{p} \max(s_{\vartheta_1, i}, s_{\vartheta_2, i}) \quad \text{(Formula I)}$$

wherein
ϑi is the $i^{th}$ parent
S=PF wherein P∈$R^{n\times p}$, and F∈$R^{p\times p}$ wherein R is a set of real numbers, n is the number of parents, p is a total number of loci to be considered.

In a preferred embodiment of the present method, the CGEBV is determined for at least two, at least three, at least four, or at most one, at most two or at most three phenotypic traits of interest. In another preferred embodiment of the method, the at least one phenotypic trait of interest is a quantitative trait. The trait is preferably influenced by multiple, e.g. at least 10, at least 20, at least 30, at least 40, at least 100, at least 200, at least 500, or at least 1000 genes, and/or preferably can (only) phenotypically be measured in quantitative terms (e.g. in kg, m, or L).

Although the present method is preferably used prior to actual selection and intercrossing of the selected combination of individuals, it is also envisaged that the present method may comprise step i) of (enabling) intercrossing (or interbreeding) of members of the identified or selected combination of at least three individuals, such that offspring, i.e. a next generation is obtained. In addition, it is also envisaged that the resulting offspring as obtained is intercrossed. Accordingly, the present method can be applied to more than one generation (see e.g. FIG. 3), such as to at least 2, 3, or at least 5 generations, although this may not be necessary in every situation.

As will be clear to the skilled person, the selection of the best parent subgroup finds its basis in the accurate estimation of allelic effects of chromosomal regions. Therefore, the accuracy of the applied genomic selection model ideally should be as high as possible. A way to enhance the level of accuracy of the model is to use state-of-the-art model construction methodology, to improve the quality of the phenotype data collected for the training panel, and to optimize the ratio marker density/average window of linkage disequilibrium, as well as the ratio loci contributing to the trait/number of observations in the training panel. Of course, factors like the genetic complexity and heritability of the trait of interest, genetic diversity of the training panel, the level genetic relationship between the training panel and the candidate parent panel may also influence the accuracy. A person skilled in the field of the present disclosure will have no problem in appreciating that variations in these input factors will result in models with higher or lower accuracy and that model accuracy can be determined through standard cross-validation procedures (Hastie, T., Tibshirani, R., Friedman, J. (2001); and Arlot, Sylvain; Celisse, 2010).

The breeding population of individuals used in the present method can be of different ploidy nature. For example, the population of individuals can be of a diploid, allopolyploid, or autopolyploid species. The same applies to the training population.

In the method of the present disclosure, the population of individuals preferably is a field crop, or vegetable crop, or woody fruit species, or forestry species, or plantation crop, preferably selected from the group consisting of *Arabidopsis thaliana*, Abyssinian mustard, alfalfa, barley, barrel clover, black mustard, buckwheat, canola, clover, common flax, common vetch, corn spurry, coffee, cotton, Egyptian clover, fodder beet, hemp, hop, Indian mustard, Jerusalem artichoke, maize, millet, mustard, lupin, oat, oilseed rape (*Brassica napus*), field mustard (*Brassica rapa*), opium poppy, Persian clover, potato, red clover, rye, safflower, sisal, soy bean, sugar beet, sunflower, tea, tobacco, triticale, wheat, white clover, white mustard, wild rice, winter vetch, artichoke, asparagus, asparagus beans, aubergine, beetroot, black radish, black bean, black salsify, broad bean, broccoli, Brussels sprouts, cabbage, cantaloupe, carrot, cauliflower, celery, chard, chicory, chili pepper, chinese cabbage, choi sum, common bean, corn salad, courgette, cucumber, daikon, eggplant, endive, fennel, garlic, goosefoot, green bean, Indian lettuce, kale, kidney bean, kohlrabi, leek, lettuce, lentil, lima bean, maize, melon, mizuna, napa cabbage, onion, parsnip, pea, pepper, potato, pumpkin, quinoa, radicchio, radish, rapini, red cabbage, rhubarb, runner bean, rutabaga, salad rocket, Savoy cabbage, shallot, soy bean, spinach, squash, sugar cane, swede, tomatillo, tomato, turnip, watercress, watermelon, yellow turnip, almond, apple, apricot, bird cherry, butternut, cashew, cherry, chokeberry, crabapple, filbert, greengage, hawthorn, hazel, heartnut, loquat, medlar, mirabelle prune, nectarine, peach, peacherine, pear, pecan, pistachio, plum, prune, quince, rowan, walnut, acacia, alder, Allegheny chinkapin, American beech, American chestnut, American hornbeam, ash, aspen, basswood, beech, bigtoothed, aspen, birch, bitternut hickory, black alder, black birch, black cherry, black gum, black locust, black maple, black oak, black poplar, black walnut, black willow, butternut, cedar, chestnut, chestnut oak, Chinese chestnut, Corsican pine, cottonwood, crabapple, cucumbertree, cypress, dogwood, Douglas fir, Eastern hemlock, elm, English oak, eucalyptus, European beech, European larch, European silver fir, European white birch, fir, flowering dogwood, gum, hawthorn, hornbeam, horse chestnut, hybrid poplar, Japanese chestnut, Japanese larch, larch, lodgepole pine, maple, maritime pine, mockernut hickory, Norway spruce, oak, Oregon pine, Pacific silver fir, pedunculate oak, pignut hickory, pine, pitch pine, poplar, Scots pine, sweet chestnut, red alder, red cedar, red maple, red oak, red pine, red spruce, redwood, rowan, sassafrass, Scots pine, Serbian spruce, serviceberry, shagbark hickory, silver birch, Sitka spruce, southern beech, spruce, striped maple, sugar maple, sweet birch, sweet chestnut, sycamore, tamarack, tulip tree, Western hemlock, white ash, white oak, white pine, yellow birch, banana, breadfruit, coconut, date palm, jackfruit, mango, oil palm, olive, papaya, pineapple, plantain, rubber tree and sugar palm.

In another preferred embodiment, the population of individuals is of a species selected from the group consisting of Cattle (*Bos taurus, Bos indicus*), Water buffalo (*Bubalus bubalis*), Equine (*Equus caballus*), Sheep (*Ovis aries*), Goat (*Capra hircus*), Pig (*Sus scrofa*), Chicken (*Gallus gallus*), Turkey (*Maleagris gallopavo*), Ducks (*Anas platyrhynchos, Cairina moschata*), Geese (*Anser anser domesticus, Anser cygnoides*), Pigeons (*Columba livia domestica*), Rat (*Rattus novergicus*), Mouse (*Mus musculus*), Cat (*Felis catus*), Dog (*Canis familiaris*), Rabbit (*Oryctolagus cuniculus*), Guinea pig (*Cavia porcellus*), Zebra fish (*Danio rerio*) and Fruit fly (*Drosophila melanogaster*).

In yet another preferred embodiment, the population of individuals is of a fish species selected from the group consisting of *Cyprinus carpio, Salmo salar, Oreochromis niloticus, Oncorhynchus mykiss, Ctenopharyngodon idella, Hypophthalmichthys molitrix, Gibelion catla, Cyprinus carpio, Hypophthalmichthys nobilis, Carassius carassius, Oreochromis niloticus, Pangasius pangasius* and *Labeo rohita*, or wherein the method is applied to a shrimp species selected from the group consisting of *Macrobrachium rosenbergii, Litopenaeus vannamei* and *Penaeus monodon*.

As described earlier herein, it is also envisaged that the present method may comprise step i) of (enabling) intercrossing (or interbreeding) of members of the selected combination of at least three individuals, such that offspring, i.e. a next generation is obtained. In addition, it is also envisaged that the resulting offspring as obtained is intercrossed.

In another aspect of the present disclosure, a computer-readable medium comprising instructions for performing the present method is provided. In a preferred embodiment, the attributing of step b), and steps c), d), e), f), g) and h) as a whole of the present method are computer-implemented steps and/or the present method is (partly) a computer-implemented method.

The method of the present disclosure can advantageously be used particularly for improving at least one (quantitative) phenotypic trait of interest in a breeding program.

Also foreseen is a product obtainable by the method according to the disclosure, preferably wherein the product is a plant.

EXPERIMENTAL

Starting Configuration

Figure 1:
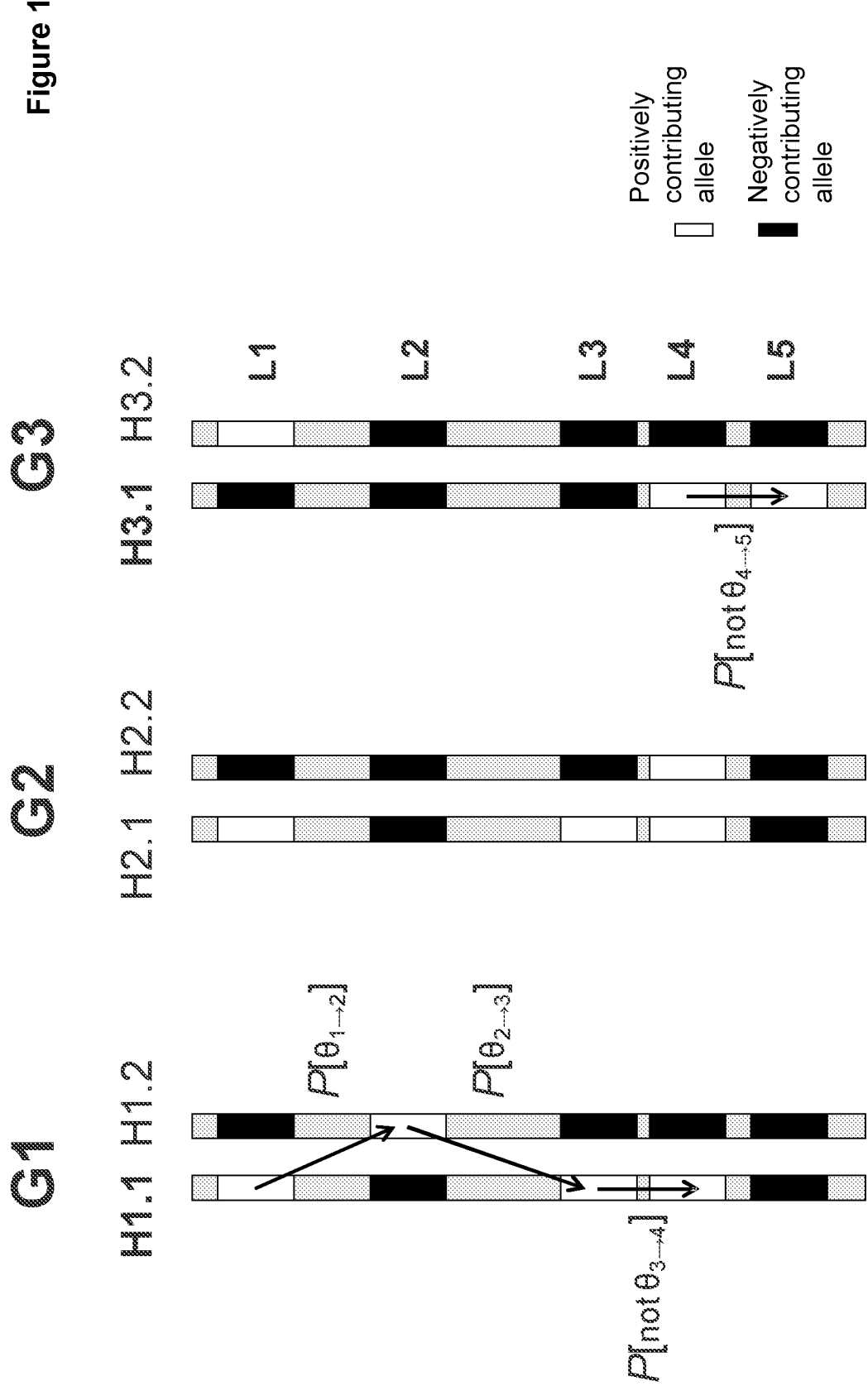
FIG. 1: Graphical representation of the selection process in a breeding population consisting of 3 diploid individuals represented by their genotypes G1-3. The individuals have been genotyped for 5 loci L1-5 and the phenotype for an individual with an particular genotype can be predicted using a mathematical genome-wide prediction model that assigns positive of negative effects on each allele occurring on the loci. The concept underlying the current disclosure involves the construction of the putative future genotype that predicts the highest phenotypic performance from haplotypes (H1.1-H3.2) occurring in the current population, or recombinants of those. In this example, the best obtainable genotype that can be obtained with a single cross is combining haplotypes H1.1 and H3.1 (indicated bold), which complement each other in locus L5 versus the others. According to the present disclosure, and extrapolating from FIG. 1, it will be clear that in larger populations, the putative genotype can be constructed analogously from haplotypes of more than two individuals.

In validation simulation experiments, directed genome wide selection (dirGWS) was compared with regular genome wide selection (regGWS). For both methods the realized progress through simulated breeding and selection was determined and compared. Both methods use the same starting material for the simulations. The model plant species used in the simulations contained 5 chromosomes with a length of 1 Morgan each. A randomly generated (parental) starting population of size N=50-1000 parents was generated. The genomic scores, i.e. the presence of specific alleles at SNP marker positions, present in the population were sampled from various plant datasets that were retrieved from the public domain. In this way realistic values for allele frequency (proportion of all copies of a gene that is made up of the allele) and inter-marker correlation were applied. Two-state allelic coding (−1/1) was applied to indicate the allelic status per allele at each locus (data derived from the dataset), where −1 means the absence of the marker allele and 1 means the presence of the marker allele. Each allele was attributed an allele substitution effect, i.e. the contribution to the phenotype of interest; the size of this effect was randomly drawn from a truncated normal distribution with mean 0 and standard deviation 1, for which all negative values were discarded. In this way each locus may contribute both positively and negatively to the trait depending on its allelic state, while the size of the contribution is determined by the effect size. Next, a multi generation breeding effort was simulated in which selected parents were intercrossed, and selection was applied on the resulting progeny in order to advance in phenotype. In our simulations phenotype was not observed directly but was implicitly determined through summation of allelic states multiplied with allele substitution effects. In order to combine, through crossing and selection, several favorable genomic regions from different sources, our simulated breeding schemes involved up to 4 cycles of crossing and selection and up to 5 different parental genotypes from the starting population. All crossings steps were simulated using commonly used methodology, abiding to Mendelian genetic rules. The approach taken to select the most optimal parents for breeding from the starting population in both methods is elaborated in the next paragraphs.

Parental Selection regGWS: for each of the parental lines a per se performance was determined based on the accumulated effects of each of the individual loci, by multiplying the allele substitution effect (drawn from a truncated Normal distribution) with the allelic state (−1 or 1) at each locus for all loci present in the genome. The lines with the highest predicted genomic performance were selected and intercrossed. In simple bi-parental simulation only two parents were involved. In more advanced simulations several breeding cycles (generations) were simulated in which in each additional cycle an additional parent was crossed with selected progeny (see below) obtained from the previous cycle. The order of the selected parents for use in next cycles followed the predicted performance ranking, i.e. the third best parent entered the breeding cycle as the third parent.

dirGWS: Parents were not selected based on their per-se performance but rather on the potential performance of their combined genomes. For all combined sets (of size 3, 4 or 5) of lines taken from the parental set of lines a predicted combined performance was estimated. The set with the highest combined performance was selected and the members of this set were used as parents for crossing.

The selection of the set with the highest combined expected performance, however, is not straightforward because cross-over frequencies and allele substitution effects should be taken into account. The selection of the best combination of parents was done as follows:

From the genetic map the cross-over frequency between two alleles can be calculated. Because two neighboring loci are in linkage disequilibrium it is likely that by passing over one locus to the next generation, the linked loci will also be transmitted to the next generation. Because two chromosomes, or linkage blocks, segregate independent from each other, no linkage drag occurs between two linkage blocks. In order to take linkage drag into account a filter was designed based on Kosambi's mapping function. Note that other mapping functions such as Haldane, or others (see Liu) can also be applied. The cross-over probability estimation between all locus pairs results in a block diagonal matrix, $F \in R^{p \times p}$ with p being the number of loci. Now with the parental genotype data matrix, $P \in R^{n \times p}$ with n being the number of parental lines, the corrected data matrix can be calculated by:

$$S = PF$$

Figure 2:
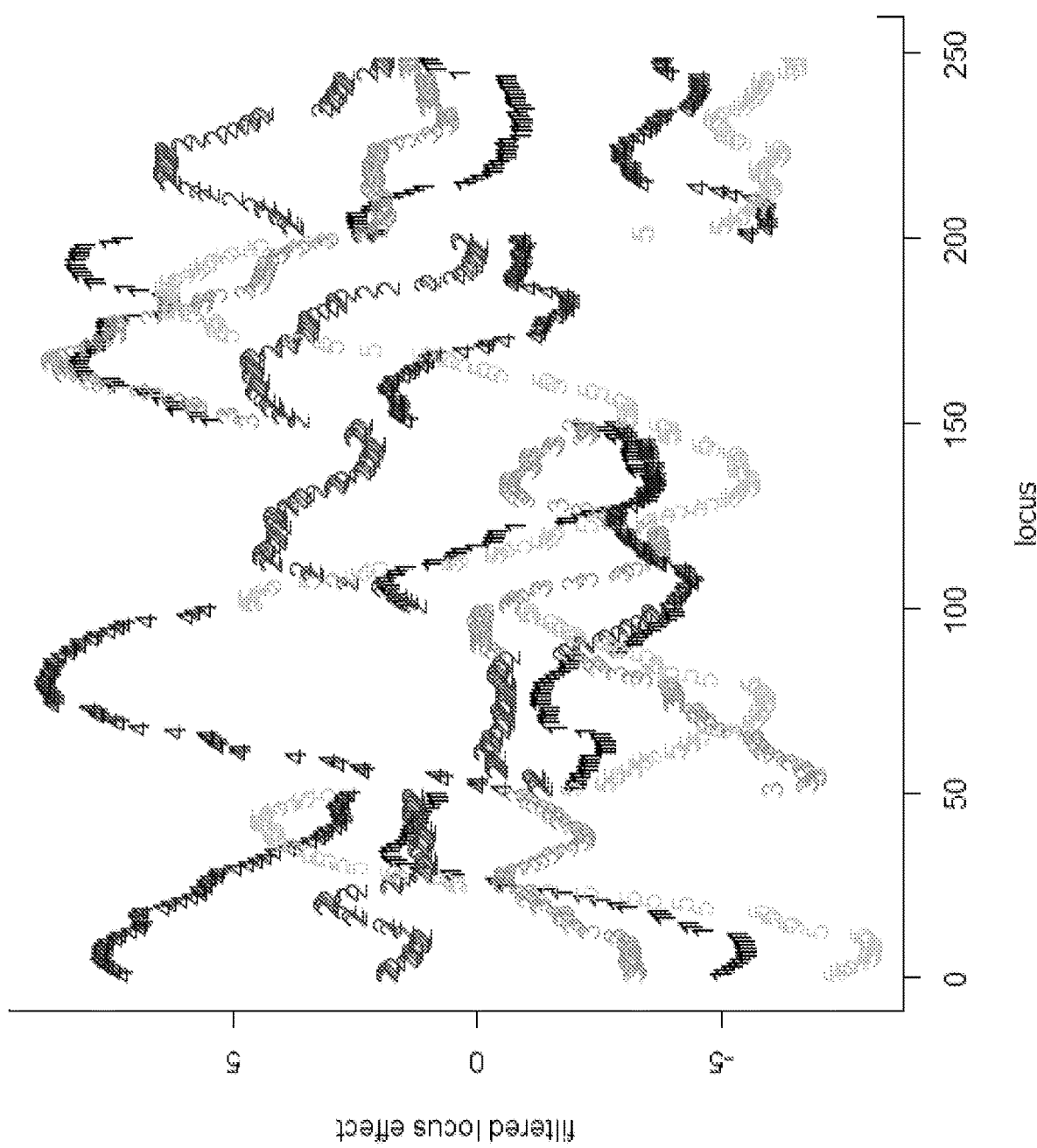
FIG. 2: An example of the filtered effects of the loci of 5 parental lines. A high value means that this part of the genome has a positive effect on the trait of interest. A combination of genotypes that yields high positive values on the entire genome is highly beneficial.

In other words, the genome-wide estimated breeding value of a parent is calculated by the total of the values for S, i.e. the corrected locus effect, of each locus. The corrected data matrix, S, then can be used as a basis for (pre)selection. In FIG. 2 an example is given for five parental lines containing 250 loci located on 5 chromosomes. From this figure it can be seen that parent 4 exceeds all other parents at the first two chromosomes (up to locus 100) but is underperforming on the other chromosomes. The relative performance of an individual was calculated in this way. The combination of parent 4, 2 and parent 1 together gives the maximum S on all chromosomes and is most likely to outperform other combinations of two or more parents.

Once the corrected population matrix S is known the best combination of parental lines can be chosen. The potential value of a parental line $\vartheta$ is taken to be $$\sum_{i=1}^{p} S_{\vartheta,i}.$$

Because there are only a limited number of cross-overs per chromosome, the regions with the highest corrected allele substitution effects can be combined while the remaining part of the genome should not have too low values since that would affect the phenotype in a negative way. The estimated value of two parental lines ($\vartheta_1$/and $\vartheta_2$) to be crossed can therefore be determined by:

$$c_{\theta_1,\theta_2} = \sum_{i=1}^{p} \max(s_{\theta_1,i}, s_{\theta_2,i})$$

$$(= CGEBV)$$

In other words, the combined genome-wide estimated breeding value (CGEBV) of two parents is calculated by taking the highest corrected locus effect S of each of the loci of the combination over the total number of loci of the combination. The subset of 2 parental lines that has the largest potential value c (=CGEBV) will be crossed. This procedure is easily extended to multiple parental lines by taking the maximum over each filtered locus for multiple parental lines. Because the procedure is limited to basic, calculation extensive matrix manipulations, many subsets can be tested. The number of subsets to be tested, however, grows with the binomial coefficient $$\binom{n}{k}$$

with k being the number of parental lines to be crossed. For n=100 and k=2 this leads to 4950 combinations which can still be easily processed. With k=5, however, the number of possible subsets grows to over 75 million. By taking a smart selection of allowed parents to select from, this number can be largely reduced. In the current examples, only those parents are selected that exceed other parents somewhere along the chromosome, by which the number of parents is reduced to approximately 20 (depending on the original population and the effect sizes of the alleles).

The number of possible combinations is then reduced to $$\binom{20}{5} = 15504$$

which, again, can all be easily calculated.

Evaluation of the Selected Parents

Figure 3:
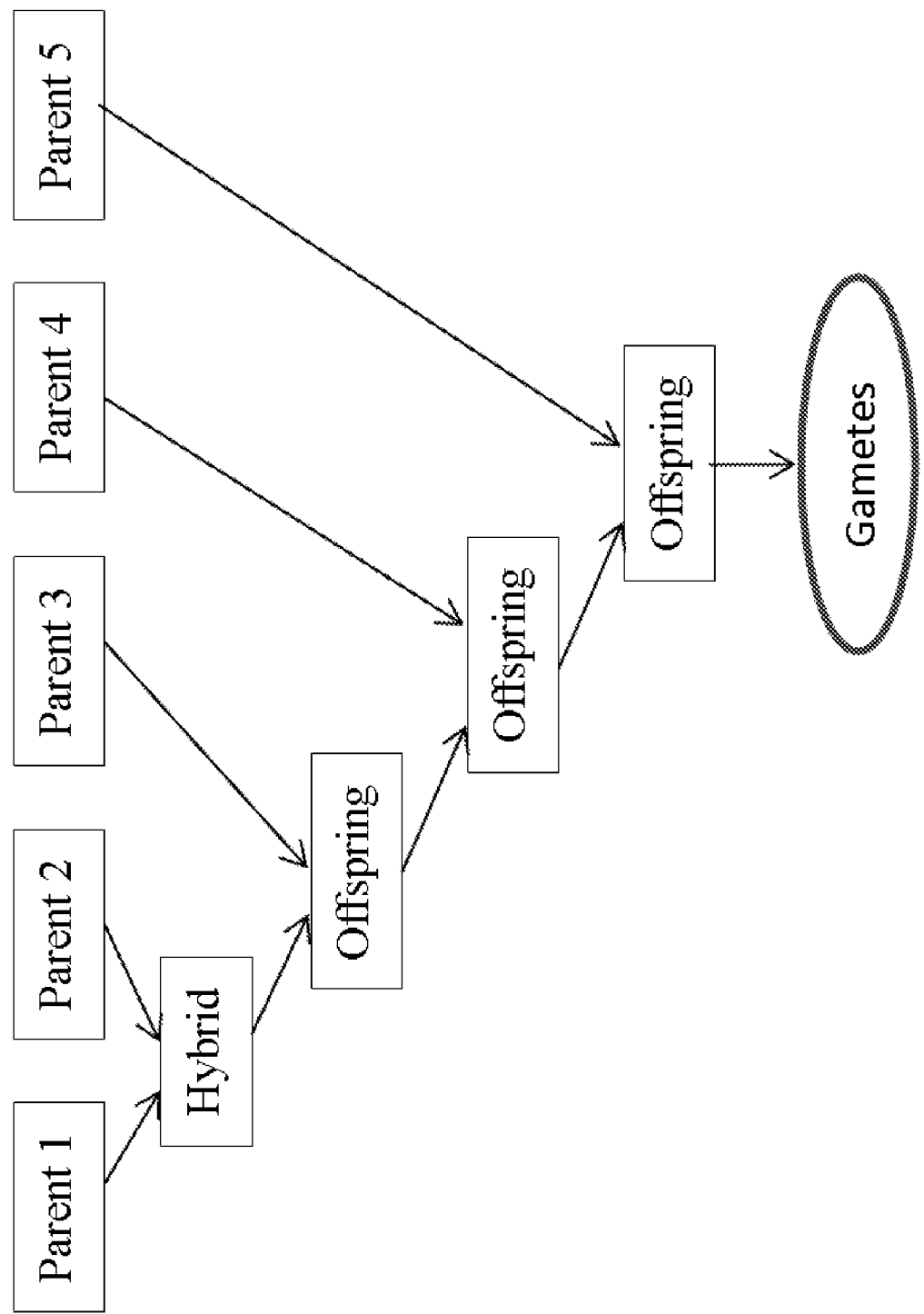
FIG. 3: Schematic representation of the crossing scheme that is used for both regGWS and dirGWS for 5 selected parents.

Stochastic simulation was used to evaluate the performance of each of the two methods. Two parents from the selected set of parents were intercrossed to generate a new hybrid genotype. This hybrid product of each cross was considered to be the base genotype from which, through stochastic simulation, 1000 gametes were generated. The generated gametes were used as a sample of the potential genetic performance of the pair of parents. These gametes were ordered by their performance, which was calculated by multiplying their allelic state at each locus (−1 or 1) with the locus genomic prediction values. The 95% percentile value of the ranked performances of the 1000 gametes was taken as a measure to judge the offspring performance. In the case that more than two parents (as a result of more than one crossing) were involved in the generation of the gamete representing the 99-100% performance percentile was also selected to represent the selected cross result, and was subsequently combined in a next breeding cycle with a gamete from the third (or 4th, 5th) selected parent. Again 1000 gametes were derived from this new cross and ordered and the 95% percentile performance value was again used to judge the performance. A schematic representation of the applied crossing scheme is represented in FIG. 3.

Figure 4:
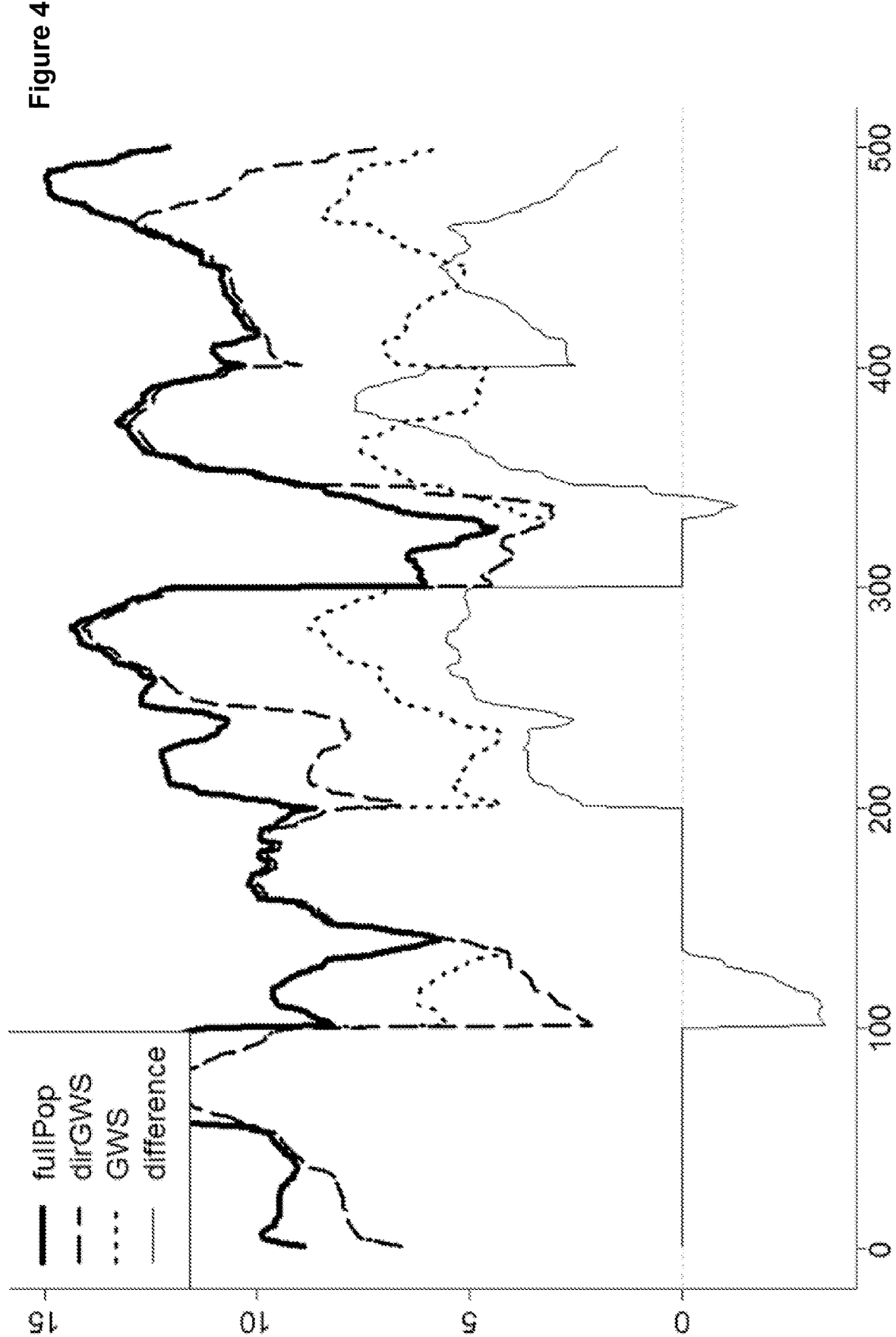
FIG. 4: Graphical representation of breeding potentials in a population. Current results were obtained by simulated GS models and real *Arabidopsis thaliana* genotype data. Visible are the potentials over five chromosomes, with plotted as a solid thick line (fullPop): the max breeding potential over an entire population of 100 individuals; The dotted line ("GWS") indicates the total potential of the selected 5 best parents; The dashed line ("dirGWS") plots the potential of the selected set of 5 best combining parents. The thin solid line at the bottom ("difference") indicates the superiority of the combined best parents over the best parents, mainly found on the chromosomes 3, 4 and 5 in this example. Please note that this simulation result is unrelated to the result example shown in FIG. 2.

FIG. 4 is a further graphical representation of genomewide breeding potentials in a population. The results of FIG. 4 were obtained by simulated GS models and real *Arabidopsis thaliana* genotype data. Visible are the potentials over five chromosomes, with plotted as a solid thick line (fullPop): the max breeding potential over an entire population of 100 individuals; The dotted line ("GWS") indicates the total potential of the selected 5 best parents; The dashed line ("dirGWS") plots the potential of the selected set of 5 best combining parents. The thin solid line at the bottom ("difference") indicates the superiority of the combined best parents over the best parents, mainly found on the chromosomes 3, 4 and 5 in this example. Please note that this simulation result is unrelated to the result example shown in FIG. 2.

Comparison of regGWS and dirGWS

Except for the initial choice of parents, the evaluation of both methods was thus performed in an identical fashion. In each round, the final values for the selected gametes of both methods were compared and it was recorded which of the methods yielded better predicted values after 2-5 cycles of breeding.

The genomic selection models were constructed using Ridge Regression (Meuwissen et al., 2001). The models used in both regGWS and dirGWS were always pairwise identical for each test round.

The entire procedure described above was repeated several hundred times to produce reliable estimates on the method comparison.

We tested this procedure for breeding schemes in which 3, 4 or 5 parents were combined. The modeled genomic effects were drawn from a truncated normal distribution with mean 0 and standard deviation 1, for which all negative values were discarded. As such all loci effects have a positive value and the sign of the contribution to the trait comes from the allelic state (−1/1). All scenarios were tested while selecting the 95% percentile best combinations.

Results

Table 3 shows the results of the dirGWS vs regGWS comparison. When three parents or more were used the directed GWS method outperformed the regular GWS selection in more than half of the cases and this frequency increased dramatically when more than three parents were involved in the breeding scheme. The increase in superiority with increasing number of parents demonstrates that the focus on an optimal combination of complementary genomic regions, as is the main idea of the directed GWS approach, indeed yields better result that a focus on per-se performance of the parents, as is typically done in classical GWS approaches.

TABLE 3 percentage in which the predicted genotypic value of the final selected genotype after 3-5 generations of selection and crossing when using directed GWS was larger than the predicted genotypic value of the final selected genotype obtained using regular GWS.

| | Fraction of cases in which dirGWS outperforms regGWS |
|---|---|
| 3 parents | 53% |
| 4 parents | 70% |
| 5 parents | 79% |

Example 1: *Arabidopsis thaliana*

A public genotype data set of the model organism *Arabidopsis thaliana* (At) was retrieved, consisting of genotype data for 250K loci of 1179 ecotypes (Horton et al., 2012). Simulated (i.e. attributed) allele substitution effects were genomewide randomly distributed over 500-2000 loci. The At lines are divided uniformly at random in a training set of 50-1000 parents, which are used to construct GS models, and a validation set (for determining the accuracy) consisting of the remaining parents. The tests were done selecting either the 99% or 100% best ranking combinations and following 2-5 breeding cycles. Each parameter (i.e. number of loci, number of parents in the training set, selecting percentage, and the number of breeding cycles) combination was repeated 200 times.

One of the presumptions of the dirGWS strategy is the availability of reasonably accurate GEBVs. This accuracy is dependent on GS model construction methodology and on training data set properties such as number of parents, the genetic diversity within the panel and the distribution of the allele substitution effects. Results for performance of dirGS vs regGS were therefore ordered to accuracy of the GS model (expressed as correlation between Breeding Values and GEBVs).

Figure 5:
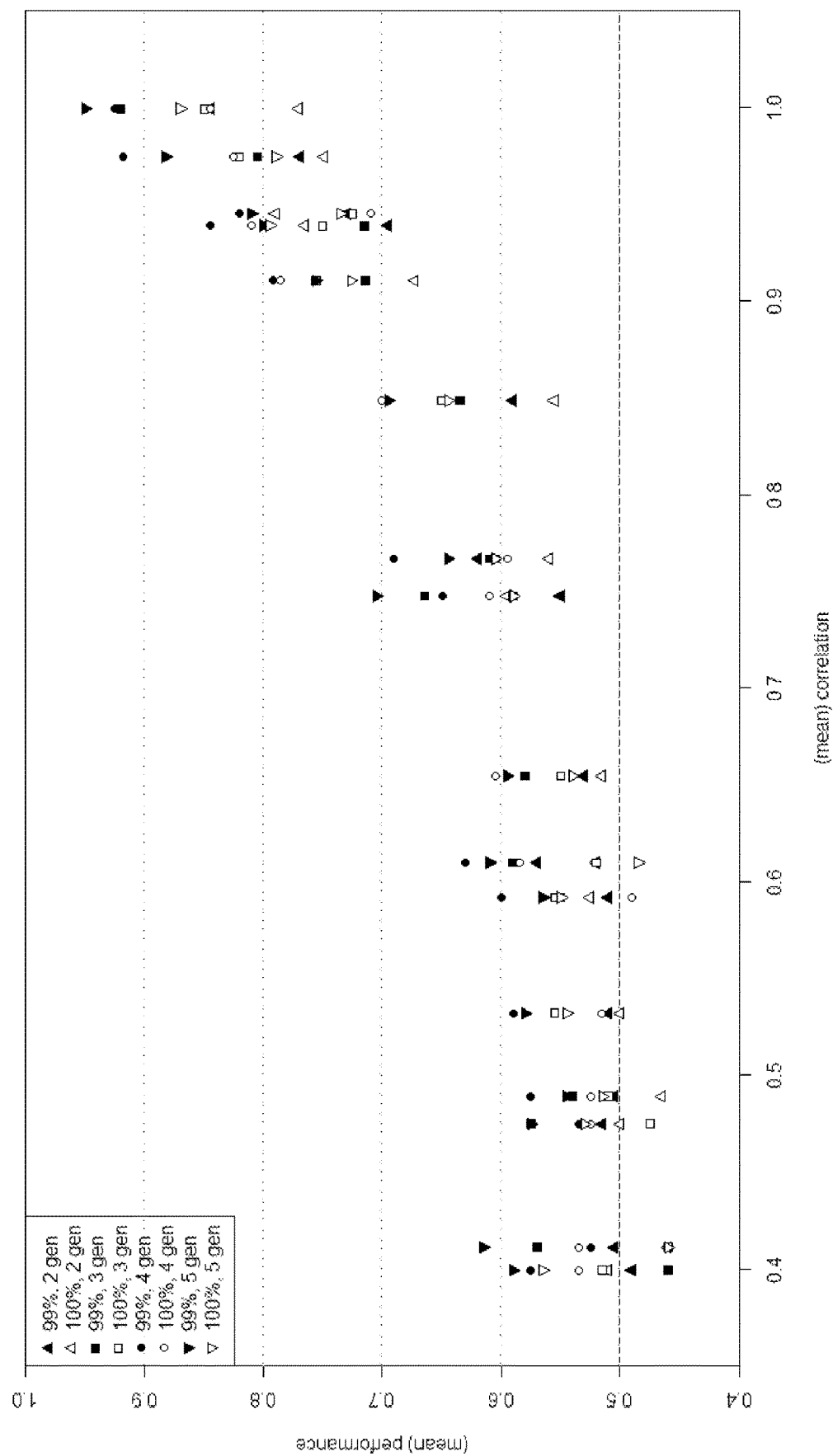
FIG. 5: Test results with the described method according to the present disclosure of directed genomic selection, in comparison to "regular" genomic selection (i.e. selection of parents with best per se GEBV). Simulations were done using *Arabidopsis thaliana* genotype data and simulated trait effects, randomly distributed over 500-2000 loci. The horizontal axis indicates the accuracy of the genomic prediction model in each situation. The vertical axis indicates the fraction of repetitions in which the performance of final result in the final breeding cycle is better in the directed GS method than in the normal GS procedure (0.6 means that in 60% of the cases directed genomic selection had a better result, and the 0.5 line indicates the regular GS performance level).

FIG. 5 shows the results of the dirGWS vs regGWS comparison, wherein the training population serves as breeding population. Directed GWS method outperformed the regular GWS selection, in particular when the GS models are more accurate (R>0.6). However, even with less accurate models, the dirGS strategy is providing better selection results, in particular when more than 2 parents are involved and the crossing scenario spans more than one generation. The increase in superiority with increasing number of parents demonstrates that the focus on an optimal combination of complementary genomic regions, according to the present invention, indeed yields better result than a focus on per-se performance of the parents, as is typically done in classical GWS approaches.

Example 2: Maize

A similar test as was done in *Arabidopsis* was performed using a Maize (*Zea mais*) genotype data for $10^6$ loci of 368 lines (Li et al., 2013). Traits were simulated by assigning allele substitution effects to 258-2015 loci. Training sets of 50-200 training parents were randomly selected. Further test procedures were similar as in the *Arabidopsis* example.

Figure 6:
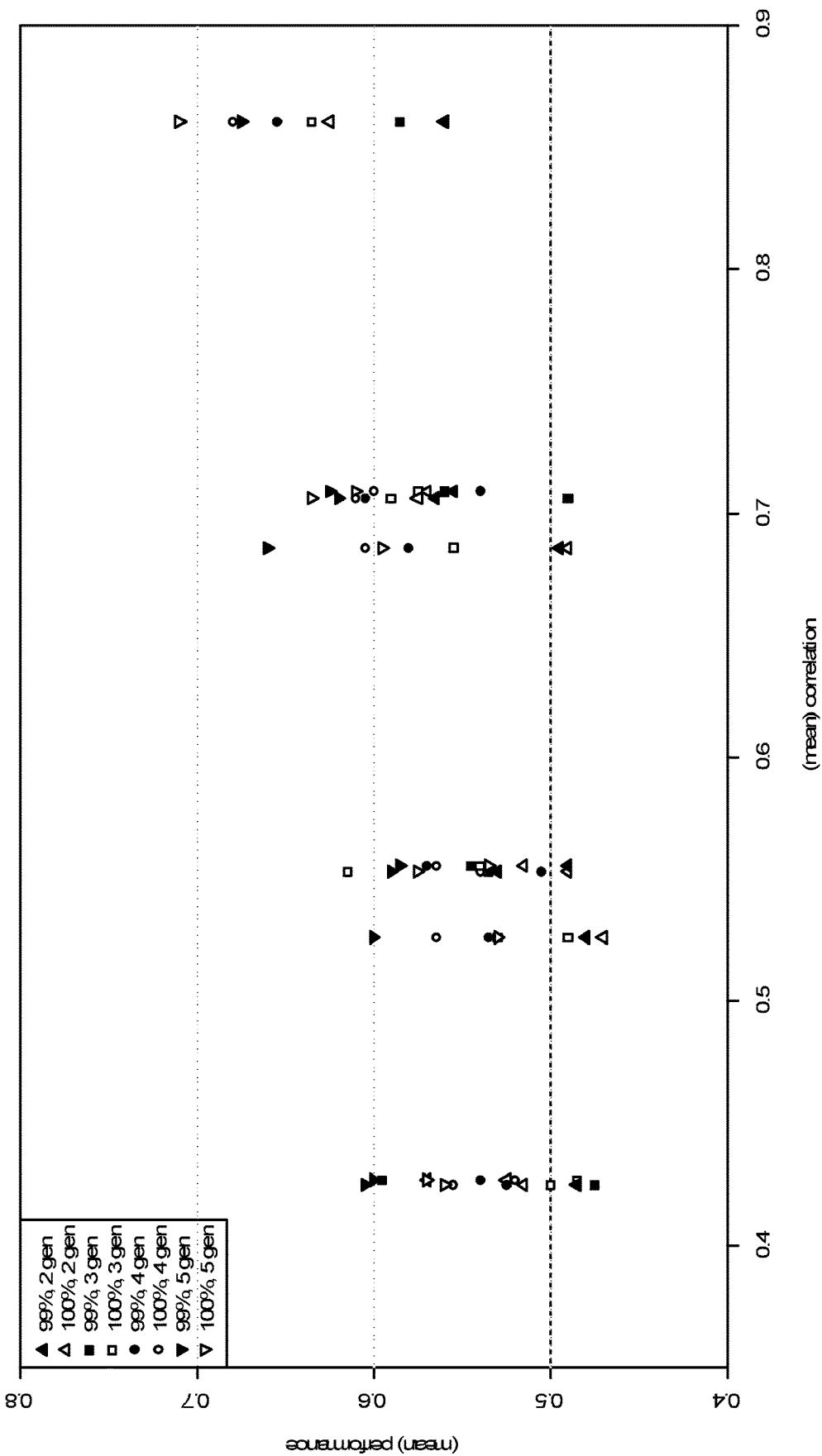
FIG. 6: as FIG. 5, but tests performed with Maize (*Zea mais*) genotype data and simulated traits.

Test results, wherein the training population serves as breeding population, shown in FIG. 6, indicate again that for most parameter combinations, the selection results are better when following the dirGS strategy, in particular when more than 2 parents are involved. The accuracy has a less dramatic effect on the overperformance of the dirGS strategy than in the previous example.

Example 3: Cucumber

A third test was conducted using Cucumber (*Cucumis sativus*) genotype data for $3.7*10^6$ loci of 115 lines (Qi et al., 2013). The set was reduced to the homozygous marker subset with no missing data (179K markers) and 86 non-identical parent lines. Trait effects were simulated on 450-1789 loci traits. GS models were constructed on training populations of 50 training parents. Further test procedures were similar as in the previous two examples.

Figure 7:
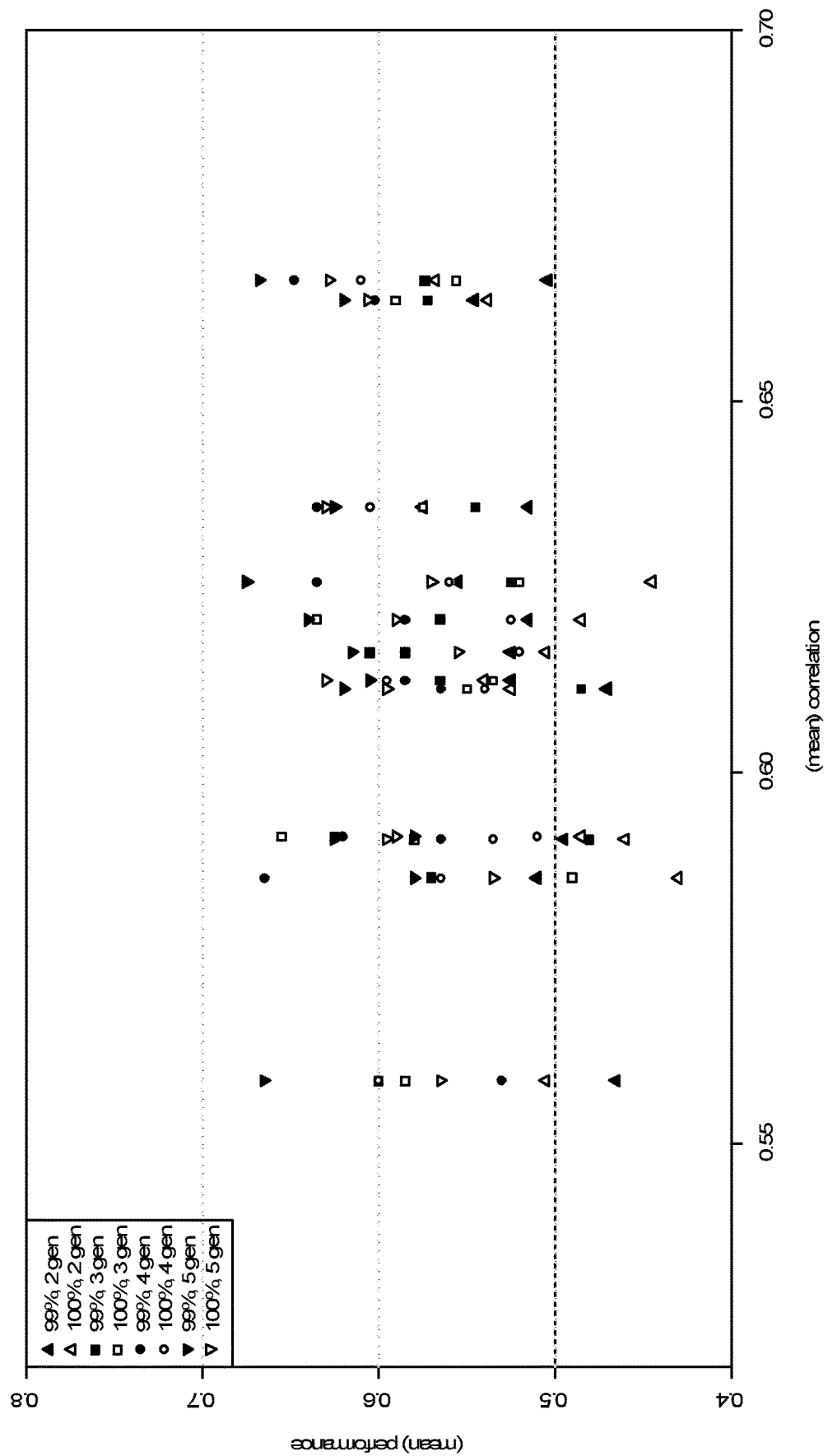
FIG. 7: as FIG. 5, but tests performed with Cucumber (*Cucumis sativus*) genotype data.

By the nature of this dataset, which contains a relative low amount of lines, it was not possible to construct very accurate models, so results were obtained for the accuracy range (0.55>R<0.67) only. Again, using the training population as breeding population, we observed an improved performance when following the dirGS strategy for most cases, and even within this rather narrow range, we observed a modest impact of model accuracy (more overperformance of dirGS is found when the accuracy is higher), see FIG. 7.

LIST OF SYMBOLS

P matrix of parental lines, each row contains a parental line, each column represents a single locus
F a block diagonal symmetric filter matrix. An entry of the $i^{th}$ row and the $j^{th}$ column represents the amount of linkage between the $i^{th}$ and the $j^{th}$ locus.
S The filtered matrix of parental lines.
R Set of real numbers
s a vector of a single parental line containing the filtered locus values of that parental line
c the potential value after crossing of two parental lines
p the total number of loci involved in selection
n the total number of parental lines involved in selection
$\vartheta_i$ $i^{th}$ parental line
k number of parental lines to be crossed

REFERENCES

Haley C. S. and Visscher P. M. (1998) Strategies to utilize marker-quantitative trait loci association. *J Dairy Sci* 81:85-97 85

Hoerl, A. E. (1959), Optimum Solution of Many Variables Equations. *Chemical Engineering Progress* 55: 69-78.
Horton M. W. et al. (2012) Genome-wide patterns of genetic variation in worldwide *Arabidopsis thaliana* accessions from the RegMap panel. *Nature Genetics* 44, 212-216
Johnson G R and Yang X S (2010) Methods and compositions for breeding plants with enhanced yield. US 2010/0037342
Meuwissen, T. H. E. et al. (2001) Prediction of Total Genetic Value Using Genome-Wide Dense Marker Maps. *Genetics* 157, 1819-1829.
Haldane, J. B. S. (1919) The combination of linkage values and the calculation of distances between the loci of linked factors. *J Genet* 8.29: 299-309.
Hastie, T., Tibshirani, R., Friedman, J. (2001). *The Elements of Statistical Learning*. New York, N.Y., USA: Springer New York Inc.
Arlot, Sylvain; Celisse, Alain. A survey of cross-validation procedures for model selection. Statistics Surveys 4 (2010), 40-79
Kishore, V. K. and Guo, Z. (2012) Methods for increasing genetic gain in a breeding population. WO 2012/075125
Kosambi, D. D. (1943) The estimation of map distances from recombination values. *Annals of Eugenics* 12.1: 172-175.
Li, H. et al. (2013) Genome-wide association study dissects the genetic architecture of oil biosynthesis in maize kernels. *Nature Genetics* 45: 43-50
Liu, B. H., Statistical Genomics, *Linkage, Mapping and QTL analysis*, CRC Press, 1998, pp. 611
Peleman, J. D., and Rouppe van der Voort, J. The challenges in Marker Assisted Breeding, CGN Eucarpia Leafy Vegetables (eds. Van Hintum, Th, J. L., Lebeda, A, Pink, D, Schut, J. W.), 2003
Qi, J et al. (2013) A genomic variation map provides insights into the genetic basis of cucumber domestication and diversity. *Nature Genetics* 45: 1510-1515.
Ragot, M. et al. (2008) Process for selecting individuals and design in a breeding program. EP 1962212

The invention claimed is:
1. A method for improving at least one phenotypic trait of interest in plant offspring by selecting combinations of at least three individuals within a breeding population of plants, wherein the combinations have for the at least one phenotypic trait of interest a higher Combined Genome-Wide Estimated Breeding Value (CGEBV) in the offspring for the at least one phenotypic trait of interest, as compared to at least 70% of the other combinations of at least three individuals within the breeding population of plants, wherein the method comprises:
(a) collecting phenotypic data for the at least one phenotypic trait of interest for each individual within a training population of individual plants, wherein the at least one phenotypic trait of interest is a quantitative trait selected from fruit size, fruit count, yield, plant height, relative growth speed, flowering time, germination rate, leaf area, disease resistance, yield components, and biochemical composition;
(b) collecting genotypic data in the form of genotypic markers for each individual within the training population using a molecular marker technique selected from the group consisting of detection of SNPs, detection of RFLPs, detection of SSR polymorphisms, detection of RAPDs, the detection of indels or CNVs, and detection of AFLP, and attributing to each allele of a plurality of loci of each individual plant, an allele substitution effect for the at least one phenotypic trait of interest;
(c) providing a genotype/phenotype relationship model for the training population of individual plants, wherein the model estimates for a given genotype of an individual plant what the quantitative contribution is of the allele substitution effects of the plurality of loci on the at least one phenotypic trait of interest;
(d) genotyping each individual plant within a breeding population in the same way as in step (b);
(e) calculating for each individual plant within the breeding population the allele substitution effect (P) for each allele of the plurality of loci by using the genotype/phenotype relationship model of step (c), and correcting said allele substitution effect for recombination probabilities with flanking loci (F), wherein a corrected allele substitution effect (S) for a locus is calculated according to formula S=PF, wherein the correction constitutes multiplying said effect with the probability that the allele is transmitted to the offspring in case said allele has a positive allele substitution effect, and multiplying said effect with the probability that the allele is not transmitted to the offspring in case said allele has a negative allele substitution effect;
(f) determining the CGEBV in the offspring for the at least one phenotypic trait of interest for each combination of at least three individual plants within the breeding population by summing for each combination of at least three individuals for each locus of the plurality of loci in the offspring the highest corrected allele substitution effects calculated in step (e), wherein the CGEBV is determined according to formula $$\Sigma_{i=1}^{P} \max(s_{\vartheta_1,i}, s_{\vartheta_2,i}, s_{\vartheta_3,i});$$

(g) selecting the combinations of at least three individual plants within the breeding population that provide for the at least one phenotypic trait of interest CGEBVs in the offspring that are higher than at least 70% of the CGEBVs in the offspring of other combinations of at least three individual plants within the breeding population,
(h) intercrossing the selected combination of at least three individual plants to produce an offspring population,
(i) measuring the value of the quantitative phenotypic trait for individual plants in the offspring population, and
(j) propagating or having propagated offspring exhibiting an improved value of the quantitative phenotypic trait as compared to the at least three individuals.

2. The method according to claim 1, wherein the combinations of at least three individuals within the breeding population provide for the at least one phenotypic trait of interest CGEBVs in the offspring that are higher than at least 80% of the CGEBVs in the offspring of other combinations of at least three individuals within the breeding population.

3. The method according to claim 1, wherein a preselection of individuals of the breeding population to be combined is made by selecting less than 30% of the individuals with the highest sum of all allele substitution effects for the plurality of loci.

4. The method according to claim 1, wherein the recombination probabilities are calculated based on genetic distances between loci, or based on aligning physical and genetic maps.

5. The method according to claim 1, wherein the training population is a specifically designed population or wherein the training population is equal to the breeding population.

6. The method according to claim 1, wherein the offspring obtained is intercrossed.

7. The method according to claim 1, wherein the method is applied to more than one generation.

8. The method according to claim 1, wherein the method is applied to a species that is diploid.

9. The method according to claim 1, wherein the method is applied to a species that is allopolyploid.

10. The method according to claim 1, wherein the method is applied to a species that is autopolyploid.

11. The method according to claim 1, wherein the breeding population of individuals is a population of plants selected from the group consisting of *Arabidopsis thaliana*, Abyssinian mustard, alfalfa, barley, barrel clover, black mustard, buckwheat, canola, clover, common flax, common vetch, corn spurry, coffee, cotton, Egyptian clover, fodder beet, hemp, hop, Indian mustard, Jerusalem artichoke, maize, millet, mustard, lupin, oat, oilseed rape (*Brassica napus*), field mustard (*Brassica rapa*), opium poppy, Persian clover, potato, red clover, rye, safflower, sisal, soy bean, sugar beet, sunflower, tea, tobacco, triticale, wheat, white clover, white mustard, wild rice, winter vetch, artichoke, asparagus, asparagus beans, aubergine, beetroot, black radish, black bean, black salsify, broad bean, broccoli, Brussels sprouts, cabbage, cantaloupe, carrot, cauliflower, celery, chard, chicory, chili pepper, chinese cabbage, choi sum, common bean, corn salad, courgette, cucumber, daikon, eggplant, endive, fennel, garlic, goosefoot, green bean, Indian lettuce, kale, kidney bean, kohlrabi, leek, lettuce, lentil, lima bean, maize, melon, mizuna, napa cabbage, onion, parsnip, pea, pepper, potato, pumpkin, quinoa, radicchio, radish, rapini, red cabbage, rhubarb, runner bean, rutabaga, salad rocket, Savoy cabbage, shallot, soy bean, spinach, squash, sugar cane, swede, tomatillo, tomato, turnip, watercress, watermelon, yellow turnip, almond, apple, apricot, bird cherry, butternut, cashew, cherry, chokeberry, crabapple, filbert, greengage, hawthorn, hazel, heartnut, loquat, medlar, mirabelle prune, nectarine, peach, peacherine, pear, pecan, pistachio, plum, prune, quince, rowan, walnut, acacia, alder, Allegheny chinkapin, American beech, American chestnut, American hornbeam, ash, aspen, basswood, beech, bigtoothed, aspen, birch, bitternut hickory, black alder, black birch, black cherry, black gum, black locust, black maple, black oak, black poplar, black walnut, black willow, butternut, cedar, chestnut, chestnut oak, Chinese chestnut, Corsican pine, cottonwood, crabapple, cucumbertree, cypress, dogwood, Douglas fir, Eastern hemlock, elm, English oak, eucalyptus, European beech, European larch, European silver fir, European white birch, fir, flowering dogwood, gum, hawthorn, hornbeam, horse chestnut, hybrid poplar, Japanese chestnut, Japanese larch, larch, lodgepole pine, maple, maritime pine, mockernut hickory, Norway spruce, oak, Oregon pine, Pacific silver fir, pedunculate oak, pignut hickory, pine, pitch pine, poplar, Scots pine, sweet chestnut, red alder, red cedar, red maple, red oak, red pine, red spruce, redwood, rowan, sassafras, Scots pine, Serbian spruce, serviceberry, shagbark hickory, silver birch, Sitka spruce, southern beech, spruce, striped maple, sugar maple, sweet birch, sweet chestnut, sycamore, tamarack, tulip tree, Western hemlock, white ash, white oak, white pine, yellow birch, banana, breadfruit, coconut, date palm, jackfruit, mango, oil palm, olive, papaya, pineapple, plantain, rubber tree and sugar palm.

12. The method according to claim 11, wherein the breeding population of individuals is a population of cucumber.

13. The method according to claim 1, wherein the genotypic data is collected in the form of $10^4$ to $10^5$ genotypic markers.

14. The method according to claim 1, wherein the improved value of the quantitative phenotypic trait of the propagated offspring is an increase in fruit count as compared to the at least three individuals.

* * * * *